(12) United States Patent
Marucci et al.

(10) Patent No.: US 6,582,451 B1  
(45) Date of Patent: Jun. 24, 2003

(54) DEVICE FOR USE IN SURGERY

(75) Inventors: Damian Delio Marucci, Coogee (AU); John Andrew Cartmill, Cammerary (AU); William Robert Walsh, Maroubra (AU)

(73) Assignees: The University of Sydney, Sydney (AU); Unisearch Limited, Sydney (AU)

( * ) Notice: Subject to any disclaimer, the term of this patent is extended or adjusted under 35 U.S.C. 154(b) by 0 days.

(21) Appl. No.: 09/936,606

(22) PCT Filed: Mar. 16, 2000

(86) PCT No.: PCT/AU00/00195  
§ 371 (c)(1), (2), (4) Date: Jan. 28, 2002

(87) PCT Pub. No.: WO00/54662  
PCT Pub. Date: Sep. 21, 2000

(30) Foreign Application Priority Data

Mar. 16, 1999 (AU) .............................................. PP 9241  
Jun. 11, 1999 (AU) .............................................. PP 0927

(51) Int. Cl.⁷ .............................................. A61B 17/28
(52) U.S. Cl. .............................................. 606/207
(58) Field of Search .............................................. 606/151–158, 606/205, 206, 207, 208, 209, 210, 211, 139, 138, 147, 148, 144, 145, 80–96; 600/566, 567, 564, 104, 105, 135, 121, 201, 203, 210, 213–217

(56) References Cited

U.S. PATENT DOCUMENTS

| | | |
|---|---|---|
| 4,038,987 A | 8/1977 | Komiya |
| 4,721,116 A * | 1/1988 | Schintgen et al. .......... 600/564 |
| 5,122,130 A | 6/1992 | Keller |
| 5,527,339 A | 6/1996 | Koscher et al. |
| 5,575,793 A | 11/1996 | Carls et al. |
| 5,618,307 A | 4/1997 | Donlon et al. |
| 5,690,673 A | 11/1997 | Koscher et al. |
| 5,735,849 A | 4/1998 | Baden et al. |
| 5,749,893 A | 5/1998 | Vidal et al. |
| 5,772,676 A | 6/1998 | Cuschieri et al. |
| 5,795,325 A | 8/1998 | Valley et al. |
| 5,810,865 A | 9/1998 | Koscher et al. |
| 5,853,412 A * | 12/1998 | Mayenberger ............... 606/51 |
| 5,911,702 A | 6/1999 | Romley et al. |
| 5,921,996 A | 7/1999 | Sherman |
| 5,928,251 A | 7/1999 | Aranyi et al. |
| 5,928,253 A | 7/1999 | Sherman et al. |
| 6,033,424 A * | 3/2000 | Ouchi ........................ 606/205 |
| 6,036,706 A | 3/2000 | Morejohn et al. |
| 6,042,563 A | 3/2000 | Morejohn et al. |
| 6,071,271 A | 6/2000 | Baker et al. |
| 6,146,394 A | 11/2000 | Morejohn et al. |
| 6,152,141 A | 11/2000 | Stevens et al. |
| 6,182,664 B1 | 2/2001 | Cosgrove |
| 6,261,307 B1 * | 7/2001 | Yoon et al. ................. 606/205 |

FOREIGN PATENT DOCUMENTS

DE 4412171 A1 10/1995  
EP 0503662 B1 3/1992

* cited by examiner

Primary Examiner—Michael J. Milano  
Assistant Examiner—Vy Q. Bui  
(74) Attorney, Agent, or Firm—Jonathan Alan Quine; Quine Intellectual Property Law Group, P.C.; Gwynedd Warren

(57) ABSTRACT

The instrument to manipulate the tissue of a body of a patient has jaws (15a, 15b) that move away from each other in a parallel motion. The artiuclating means for the jaws comprises a scissor type linkage (24a, 24b, 25a, 25b) constrained within a support (11). Movement of the jaws (15a, 15b) is enacted through the reciprocating rod (14) acting upon one end of said scissors linkage.

45 Claims, 18 Drawing Sheets

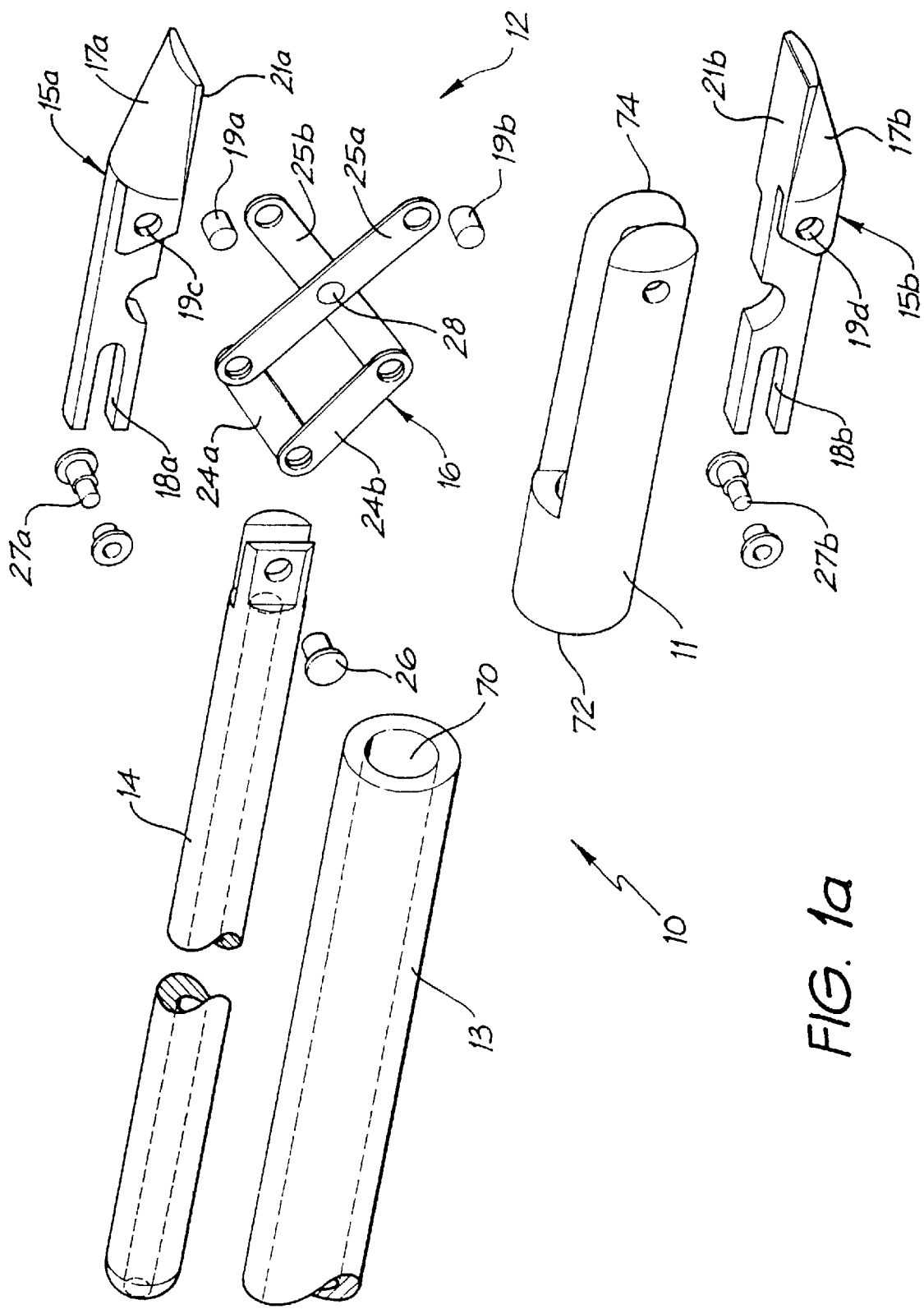

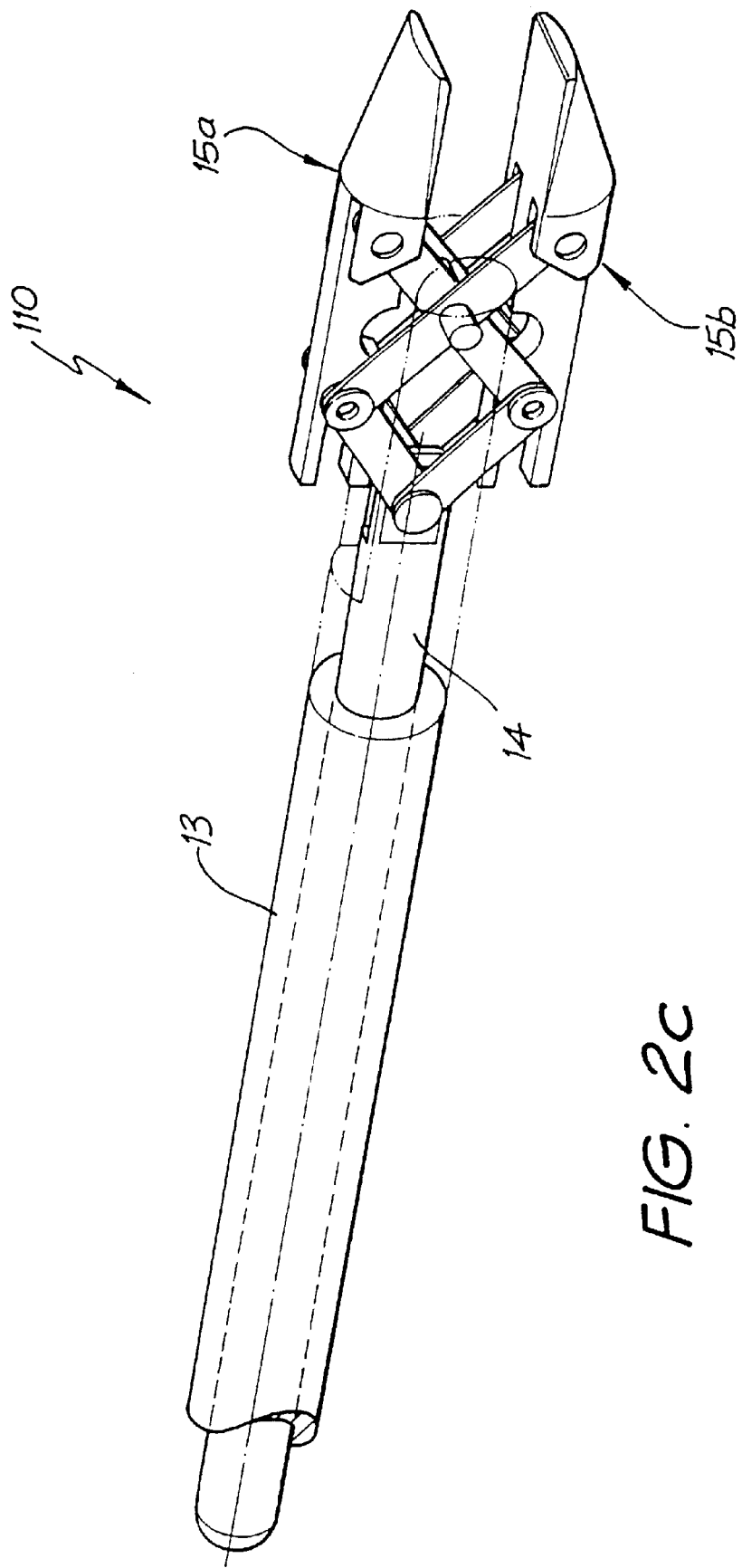

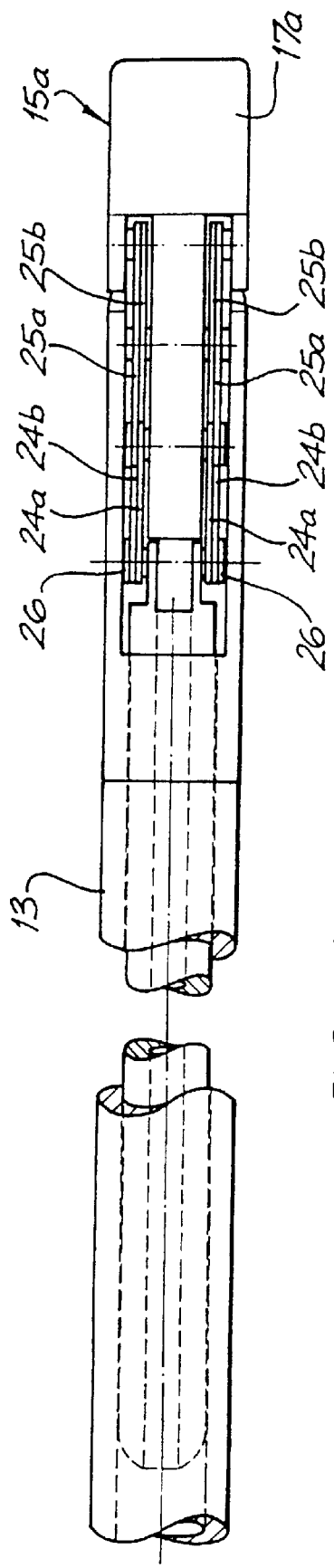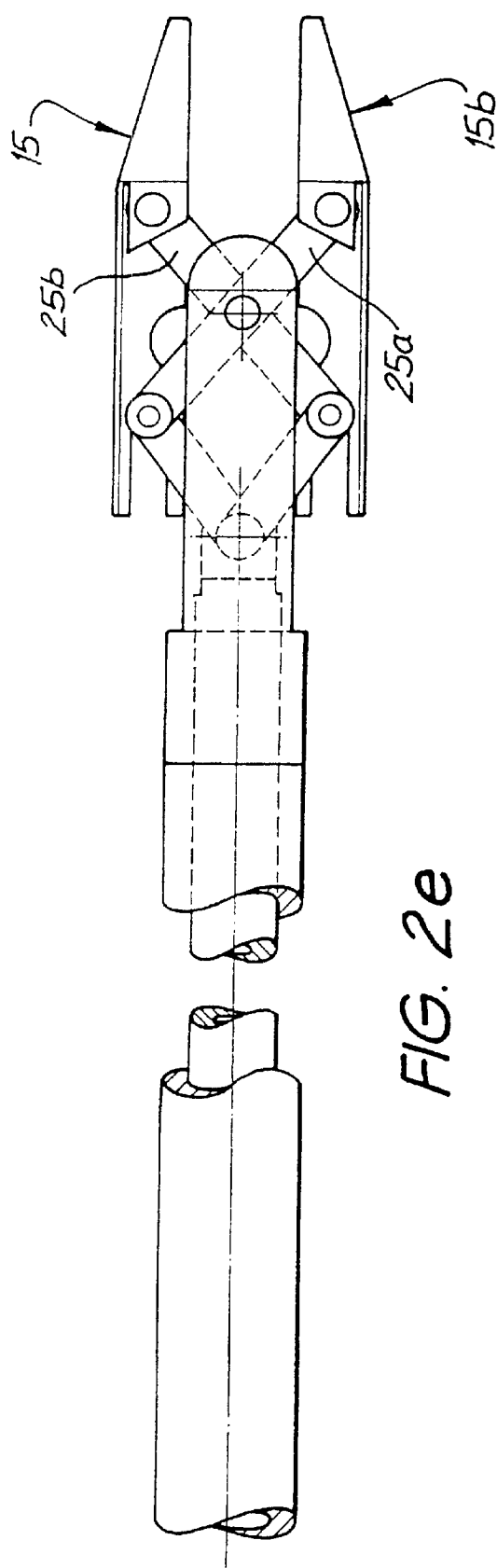
FIG. 2d
FIG. 2e

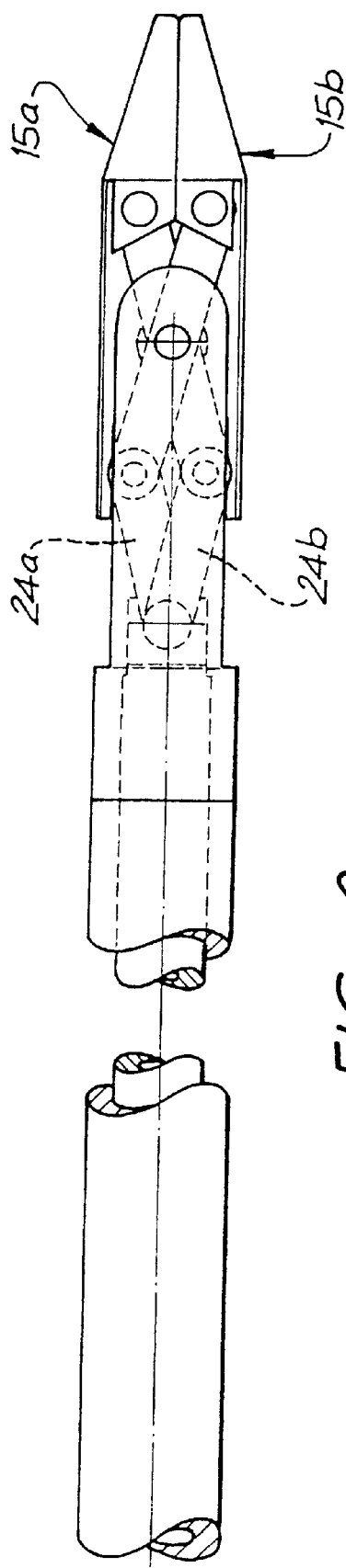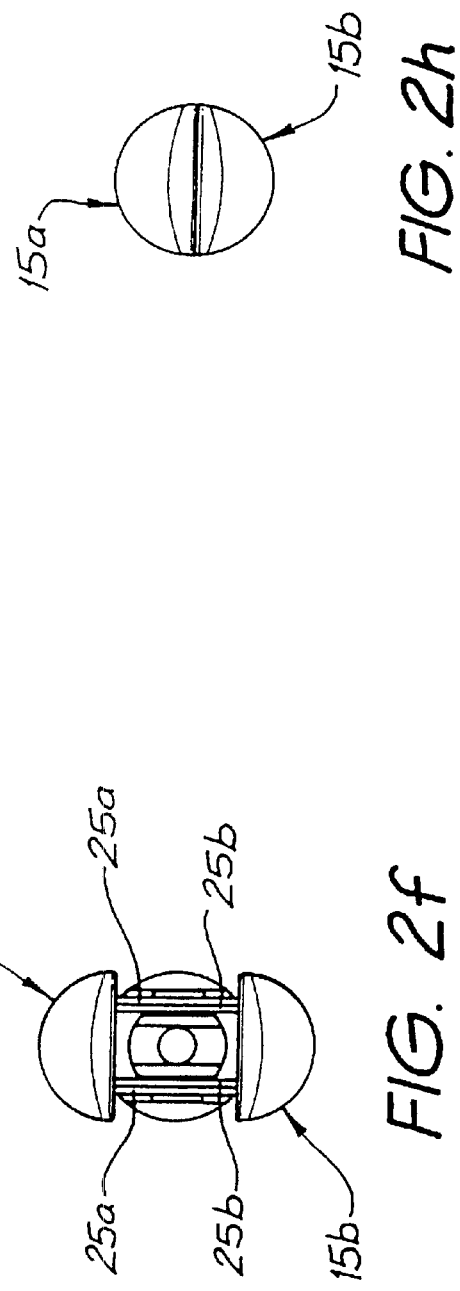
FIG. 2g
FIG. 2h
FIG. 2f

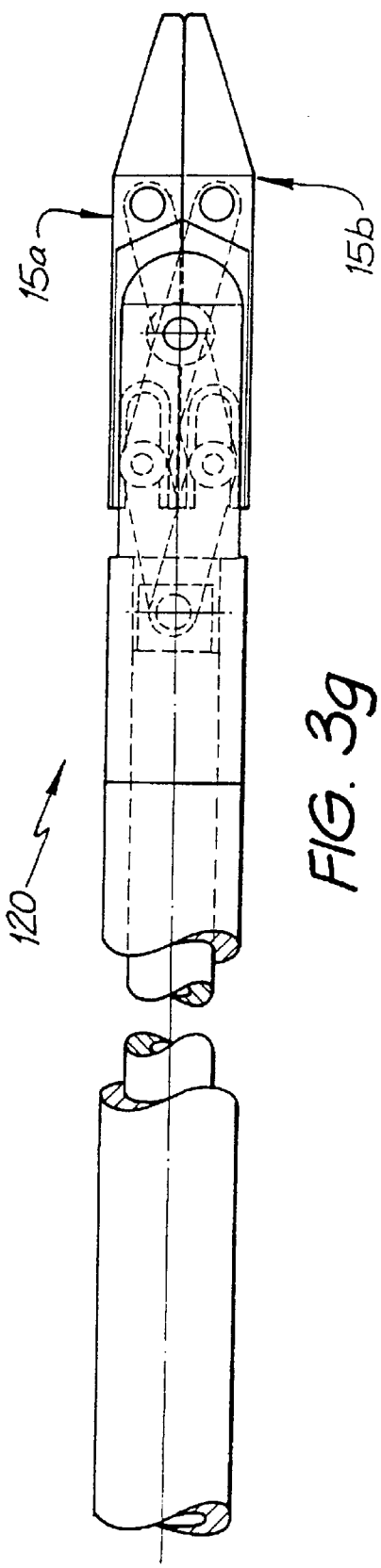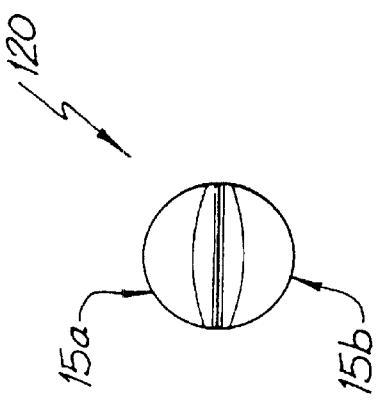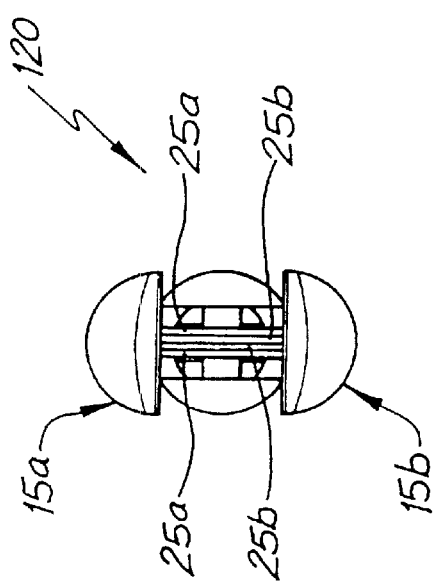

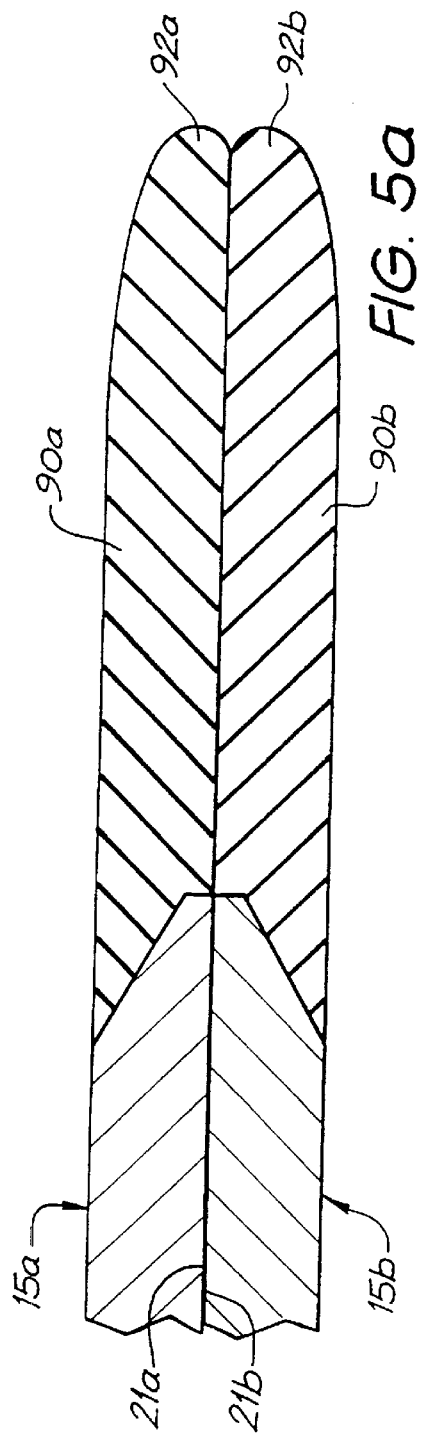
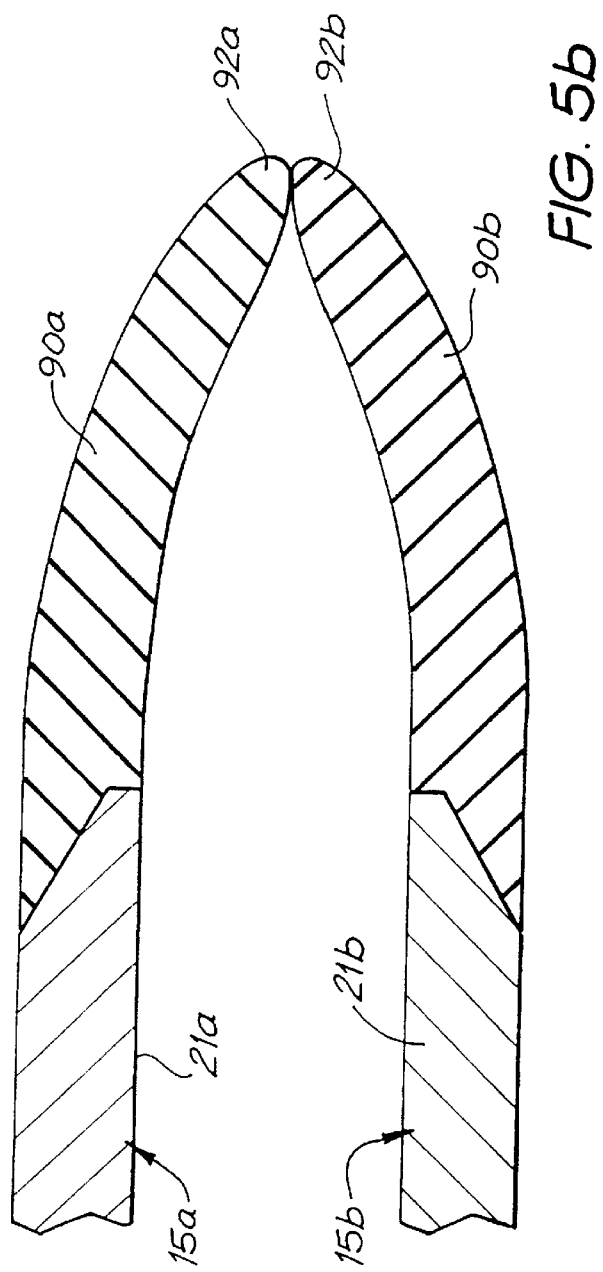

DEVICE FOR USE IN SURGERY

FIELD OF THE INVENTION

The present invention relates generally to a surgical instrument for manipulating, grasping, cutting, cauterising, clipping, stapling, spreading, retracting or clamping tissues in the body of a patient or animal, or as a platform for diagnostic and therapeutic modalities and for applications to achieve cutting, haemostasis, sealing and joining of tissues. More specifically, the present invention relates to such a surgical instrument when adapted for use in the performance of minimally invasive or open procedures.

BACKGROUND OF THE INVENTION

It is well known to use surgical instruments with a jaw structure for manipulating, grasping, cutting, cauterising, clipping, stapling, spreading, retracting and/or clamping tissues in the body of a patient or animal during surgical procedures. Such instruments are also used in procedures involving minimally invasive intervention, such as arthroscopy, endoscopy, endoscopic spinal surgery, endoscopic neurosurgery, laparoscopy and thoracoscopy, among others.

Generally, the jaw members of such surgical instruments are brought relatively towards and away from each other through articulation of the respective proximal ends of the jaw members about a single pivot point or hinge. However, there are also instances where the jaw structure has been manufactured to incorporate more than one pivot point. Nevertheless, in these devices, the jaw opens in such a way that the respective distal ends of the jaw members move relatively apart while the respective proximal ends articulate about the pivot point. This scissor-like action, while widely utilised in surgical instruments, poses a number of problems which require further discussion.

On opening of the jaw, the distance between the distal ends of the jaw members exceeds the distance between the proximal ends. When an instrument having such a jaw is then used to grip a section of body tissue, the gripping pressure made on the tissue adjacent the proximal end exceeds that made by the jaw members adjacent their distal ends. In circumstances where it is critical that the section of tissue between the distal ends of the jaw members be gripped firmly, the risk of unintentional trauma to the tissue positioned adjacent the respective proximal ends of the instrument's jaw members is very high. This is particularly the case in endoscopic procedures where visibility and accessibility is limited. Further, the pivotal action can lead to tissue positioned between the jaw members being squeezed out of the jaw away from the pivot point.

One alternative jaw arrangement that is adapted to overcome the problem of scissor-like jaw structures is described in U.S. Pat. No. 5,749.893 to Vidal et al. This patent describes a surgical instrument in which the jaw members are capable of moving in a substantially parallel relation between a fully open position and an approximated position where the jaws are closed together. In one embodiment, the jaws of this structure are pivotally mounted such that its lower jaw may pivot with respect to the upper jaw. While a substantially parallel relation between the jaw members is obtained using this structure, it is not capable of maintaining a parallel relation through the entire range of motion of the jaw members.

The present invention provides a jaw structure that addresses the problems of scissor-like instruments.

SUMMARY OF THE INVENTION

In a first aspect, the present invention is a device for manipulating tissues in the body of a patient or animal, the device including:

support means:

a reciprocating member which moves relative to the support means;

an articulated jaw structure having:

a first and at least a second jaw member, each jaw member having a proximal end and a constraining surface adjacent its proximal end: and an articulating means for articulating the jaw members in response to reciprocation of the reciprocating member, the articulating means including:

first and second connecting members, and at least first and second articulation members, wherein the first and second connecting members are each connected by a first pivotal connection to the reciprocating member and extend to respective second and third pivotal connections, and the first and second articulation members are connected together intermediate their respective ends by a fourth pivotal connection mounted to the support means, the first articulation member extending from said second pivotal connection to a fifth pivotal connection with the second jaw member distal its proximal end, and the second articulation member extending from said third pivotal connection to a sixth pivotal connection with the first jaw member distal its proximal end, the second pivotal connection being adapted to engage the constraining surface of the first jaw member and the third pivotal connection being adapted to engage the constraining surface of the second jaw member, such that on relative movement of the reciprocating member towards or away from the fourth pivotal connection, the second and third pivotal connections are caused to move relatively away from or towards one another, so moving the entire jaw members relatively away from or towards one another.

The configuration of the articulating means according to the above aspect enables relative movement of the reciprocating member towards or away from the fourth pivotal connection. As a result of such movement, the second and third pivotal connections are caused to move relatively away from or towards one another, so changing the configuration of the articulating means in a concertina fashion from a first to at least a second orientation. When in the first orientation, corresponding points on each of the jaw members are separated by a first distance; and similarly, when in the second orientation, corresponding points on each of the jaw members are separated by a second different distance. Two particular points on the respective jaw members are taken to be corresponding points as defined herein if, throughout the entire range of movement of the two jaw members, those two particular points maintain a constant positional relationship with one another. That is, those two particular points will always come back to the same relational positions with respect to one another, once the jaw members are moved back into the position which they were in when those two particular points were originally identified.

In the above aspect, reciprocation of the reciprocating member can result in movement of the jaw members in parallel relation to one another. In a preferred embodiment of the invention, both jaw members will move equal distances away from and towards each other. In an alternative embodiment, however, one jaw member may remain stationary while the other jaw member moves relative to it. In such an embodiment, the jaw member which remains stationary may be connected to, or be an integral part of, the support means.

In a still further embodiment, the surfaces of the two jaw members which face one another can be parallel. Alternatively, the faces can maintain an angular relationship with respect to one another, irrespective of the particular moving relationship between the two jaw members. These latter embodiments may, in fact, relate to the specific shape chosen for the jaw members, and it is noteworthy that all possible varieties of shape chosen for the individual jaw members fall within the scope of this invention.

The present invention can utilise a mechanism to achieve movement of the jaw members relatively toward and relatively away from one another, but wherein such movement is not restricted to being parallel. In such an embodiment, for example, an additional constraining surface may be incorporated into each of the articulation members. Accordingly, the pivotal connection between said articulation members can be adapted to engage both of their respective constraining surfaces simultaneously. While reciprocation of the reciprocating member will cause relative movement between the jaw members, the angular relationship of the latter will depend on where the pivotal connection of the two articulation members is located in both constraining surfaces of said articulation members.

In such an embodiment, the position of the pivotal connection connecting the articulation members could be adjusted in a number of ways. For example, such adjustment could be achieved through manipulation of an adjustment means capable of changing the positional relationship between said pivotal connection and the support means. Such adjustment means could take the form of a pin extending from said pivotal connection to a point of engagement with a slot, or other similar constraining surface, in the support means; wherein the pin would be slidably engaged with the slot or other appropriate constraining surface. Alternatively, the adjustment means could be such that an extension from the pivotal connection between the articulation members is threadably attached to an elongate member; which itself extends through or alongside a lumen in the reciprocating member, and has a fixed positional relationship with the support means. In this embodiment of the invention, rotation of the elongate member results in movement of said pivotal connection relative to both slots of the articulation members simultaneously.

Consequently, when the pivotal connection of the articulation members is located in the centre of both of their respective slots simultaneously, the jaw members move in parallel relation to one another; and when said pivotal connection is in a different location within the slots of the articulation members, movement of the jaw members by reciprocation of the reciprocating member will result in the jaw members arcing out a radius of curvature with respect to one another.

Indeed, in these embodiments just disclosed, the moving relationship between the jaw members can be changed at any time by adjusting the position of the pivotal connection within the two slots of the articulation members. This may be advantageous in situations where the surgeon wishes to change the relative orientation of the jaw members for either precision gripping or retraction.

The device according to this invention may be used in a range of surgical procedures. However, it is of particular value when used in the performance of minimally invasive surgery. While the device is capable of grasping and manipulating many different kinds of tissues in the body of a patient in a minimal access setting, it can also be used to clamp vessels during open procedures, for example, the performance of a vascular anastomosis. In this embodiment, the device allows for an even application of pressure to the vessel wall. It also minimises the potential damage to adjacent structures as the jaw members only have to open as wide as the diameter of the vessel, and no further, in order to receive the vessel.

In addition, the use of the device is not limited to those applications only. It may, for example, further be used as a dilating means, capable of dilating any vessel in the body of a patient including, but not limited to, those vessels comprising the vasculature, the hepatobiliary tract and the genitouriniary tract: or as a delivery means, capable of delivering a particular device, such as an implant, a graft or a stent, to a desired location in the body of a patient.

The device can be used to dilate vessels or any other hollow viscus. In this embodiment, the device provides an even expansive force on the tissue through an outer surface of the jaw members. The distance between the jaw members during such dilatation provides a route for blood (or any other fluid) to flow during the procedure. In the case of angioplasty, this limits the amount of ischaemic damage done to the distal tissues, as blood flow is not interrupted. Another advantage of this mechanism as a dilating means is that the force applied to the vessel can be measured through strain gauges or other load measuring devices mounted to the articulating means.

The device in another embodiment can be used to crush and/or remove fragments of bone or soft tissue, such as an intervertebral disc.

In an embodiment of the invention where the device is to be used for manipulating, grasping, cutting, cauterising, clipping, spreading, retracting, stapling or clamping tissues during an open surgical procedure, such as a laparotomy, its size is not of particular importance. It should, however, be manufactured such that it is of an appropriate and convenient size. Where the device is to be used for manipulating, grasping, cutting, cauterising, retracting, clipping, stapling or clamping tissues during a laparoscopic, arthroscopic, or any other minimally invasive procedure, it should be adapted for incorporation into a conventional laparoscopic grasper, or other appropriate laparoscopic or minimally invasive surgical instrument, which provides a means through which a surgeon can manipulate the reciprocating member.

Minimally invasive instruments are necessarily of a small diameter. However, in one preferred embodiment of the present invention, the articulating members, connecting members and constraining surfaces of the device can be elongated such that the jaw members can separate a relatively wide distance apart. The advantage of a device according to this embodiment, wherein the jaw members are capable of opening widely once inside a cavity (whether that cavity is the abdomen, chest, knee or any other limited space within the body), is that the jaw members can open to a size capable of receiving large structures. It is, therefore, not necessary for a device according to this invention to have a large diameter in order to be capable of manipulating large organs. Indeed, in the preferred embodiment just disclosed, the jaw members of a relatively small device are capable of being moved great distances apart. This is particularly advantageous in grasping an organ for stapling and cutting.

Similarly, the ability to widely separate the jaw members is important in using the device as a retractor. In this preferred embodiment, the outer surfaces of the jaw members can be used to push tissue out of the way. Other instruments can then be used to manipulate the operative site, which is located in the space opened up between the jaw members.

In another preferred embodiment, the surgeon is able to gain access to the operative site via a lumen through or beside the reciprocating member; or alternatively, such access may be gained through or beside the lumen of the support means. Whilst the jaw members are acting as retractors, various devices can be passed through either or both of these lumens to manipulate the operative site between the jaw members. Such devices may include a camera, diagnostic probes, suction and irrigation means, biopsy forceps, biopsy needles or any other delivery means of diagnostic or therapeutic modalities.

In yet another preferred embodiment, the outer surfaces of the jaw members may be used to separate vertebral bodies during minimal access spinal surgery. In this embodiment, the jaw members give mechanical support to the spinal column or body structure. A cage, or other vertebral support means, can then be deployed through the lumen of the instrument into the space provided by the retracting jaws.

Note also, that in some embodiments, the device may be delivered to a site by an appropriate delivery means. The articulating means may then be locked such that the jaw members are fixed in an open position, and the device call then be detached from the delivery means and left in situ to provide ongoing mechanical retraction or support.

In a preferred embodiment, the support means comprises a cylinder with a lumen having a proximal end and a distal end. In a further embodiment, the device according to the present invention can be at least partly located within the lumen of the support means and secured thereto, at least by a pin passing through the fourth pivotal connection of the first and second articulation members. The location of the device within the lumen can be further such that at least the fourth pivotal connection between the first and second articulation members is proximate the distal end of the support means. There is, however, no particular limitation on the location of said pivotal connection with respect to the support means provided that said pivotal connection can, in some way, be secured to the support means. It may even be located at a location some distance from the distal end of the support means. Nevertheless, in any of these constructions of the device, the proximal end of the reciprocating member preferably extends proximally beyond the proximal end of the support means, and the distal ends of the jaw members preferably extend distally beyond the distal end of the support means.

In an alternative embodiment, both the distal ends of the jaw members and the distal end of the reciprocating member can be respectively proximate the distal end of the support means and distal the proximal end of the support means. In a still further embodiment, the distal ends of the jaw members can be proximate the distal end of the support means and the proximal end of the reciprocating member can be proximate the proximal end of the support means.

In a further preferred embodiment, the cross-sectional diameter of the support means may be considerably smaller than that of the embodiments described in the preceding paragraph. For example, the cross-sectional diameter of the support means can be slightly larger than that of the greatest cross-sectional length of the reciprocating member, thereby ensuring that the reciprocating movement of the latter is not restricted.

In another embodiment, the cross-sectional diameter of the support means may vary along its length. For example, the support means may gradually taper from a larger cross-sectional diameter at a region adjacent its proximal end (ie the proximal region), to a smaller cross-sectional diameter at a region adjacent its distal end (ie the distal region). In an alternative embodiment, the reverse may also occur. The tapering of the cross-sectional diameter may occur at any point along the length of the support means. It may be gradual or may occur very rapidly. In another embodiment, there may be no tapering, and the cross-sectional diameter may change from one size to another, thereby forming a circumferential step in the support means.

In an embodiment of the invention where the cross-sectional diameter of the support means is relatively small at its distal region, a slot can be provided in said distal end which is adapted to receive the connecting members and the articulation members. This ensures that movement of these latter members is unrestricted. Where the cross-sectional diameter of the distal end of the support means is large enough to encompass the entire device it is, of course, unnecessary to incorporate such a slot.

In yet a further embodiment, the distal region of the support means can be planar and in the same plane as the connecting members and articulating members. In such an embodiment, the support means can taper along its length from a cylindrical shape at its proximal region to said planar shape in its distal region. Such a construction substantially decreases the size of the device around the jaw members.

The support means can extend distally from its connection with the articulating means. This extension of the support means can act as a tissue guard to prevent tissue entering the region between the jaw members and being damaged by the articulation members on movement of the jaw members.

The jaw members, according to this invention, can have a variety of functions and, therefore, be used in a variety of ways. In one embodiment, for example, the jaw members may act as platforms for diagnostic or therapeutic modalities including, but not limited to: ultrasound, lithotripsy, radiotherapy, radiofrequency, unipolar and dipolar electrocautery, stapler-cutters and/or for the application of clips.

In a further embodiment, an outer surface of each jaw member which is likely to come into contact with body tissues can have a radius of curvature. Consequently, when the device has its jaw members in a closed position, the distal end of the device will preferably be smoothly rounded, and, therefore, unlikely to do damage when advanced into contact with tissues. Such a radius of curvature for the outer surfaces of the jaw members would also be of considerable benefit in circumstances where the device is being used to retract tissues (ie spread tissues apart) in order to gain access to the tissue between the jaws; or in circumstances where the device is being used as a means to dilate a vessel. In another embodiment of the invention, the surfaces of the jaw members which face one another (ie the surfaces between which tissue will be grasped) can comprise a curved surface or have a radius of curvature to minimise tissue trauma.

The curved surface can constitute a portion of spherical surface, an oblate spherical surface, a cylindrical surface, a parabolic surface, or any other curved surface which meets the requirement of ensuring that the device has no sharp edges.

The material from which at least the surfaces of the jaw members of the device are constructed can be such that it reflects the likely viscoelastic properties of the tissue into which the device is to come into contact during an operation. For example, the stiffness of such material comprising at least the surfaces of the jaw members of the device when adapted to manipulate stiff tissue should be more than that comprising the surfaces of jaw members on the device when adapted to manipulate a relatively less stiff tissue. Where the device is manufactured with surfaces of its jaw members having a radius of curvature, such surfaces could be made of a viscoelastic or compliant material, such as silicone, or could be capped with an appropriately moulded section of such material.

Where the device is specifically to be used for grasping or clamping tissues, a surface of each of the jaw members may be lined with a plurality of gripping members. The surfaces of the jaw members to be lined by such gripping members are those between which tissue will be grasped or clamped, namely, the surface of each of the jaw members which face one another.

One preferable pattern for the gripping members can comprise a series of parallel rows of gripping members cross-hatched with a further series of parallel rows of gripping members, such that there is an angle between the perpendicular axes of the two rows. This particular pattern would assist to prevent "marching" of the device along the walls of an artery which it is being used to clamp during, for example, an arteriotomy. It is important to note, however, that the scope of this invention is not limited to circumstances wherein gripping members are of the particular shape, and/or line the surfaces of the jaw members with the particular pattern, just disclosed. Indeed, alternative embodiments of the invention include gripping members of all shapes, which can be arranged to line the appropriate surfaces of the jaw members in an unlimited variety of patterns.

In a further preferred embodiment, an additional or alternative means for grasping or clamping tissues between the jaw members can be utilised. One or both of the jaw members can have a chamber, an opening at the proximal end and a plurality of perforations on the surface of the jaw member that opposes the corresponding surface of the other jaw member. Accordingly, the space between the jaw members, the chamber inside of one or both jaw members and an area proximate the proximal end of the jaw members are all in fluid communication with one another. In such an embodiment, tissue can be caused to remain in contact with the surface of the jaw member having a plurality of perforations by creating a negative pressure inside the jaw member. This can be achieved by applying suction to the chamber through a catheter, or other appropriate device, which is attached to the opening at the proximal end of one or both jaw members. The suction catheter would access the jaw member either through a lumen within or beside the reciprocating member or a lumen within or beside the support means. The amount of suction applied to the tissue could be regulated by the surgeon. Additionally, a tensile (suction) force, as opposed to a compressive force would be used to manipulate tissue. This would minimise tissue trauma. Similarly, irrigation could be applied to the operative site or tissue being manipulated by passing irrigation fluid through the same or an adjacent catheter positioned within the device.

In another preferred embodiment of the invention, the construction of the articulating means is such that the connecting members and the articulation members are pivotally attached in a configuration in which there are more than two connecting members and more than two articulation members. However, subject to making a few minor practical alterations to the design, an articulating means comprising any even number (greater than two) of articulation members will provide a functional mechanism which complies with the disclosure of this particular embodiment.

Each constraining surface is preferably located adjacent the proximal end of its respective jaw member. Each constraining surface can constitute a slot which, when the device is viewed in side elevation, has a longitudinal axis and two ends. Each end of the slot can have a radius of curvature. It is further preferable for the longitudinal axis of each constraining surface to be in the same plane as a longitudinal axis of the jaw member to which it is connected, or with which it forms an integral part. The slot may be substantially rectangular, or any other shape which will provide for longitudinal movement of the pivotal connection between the corresponding connection member and articulation member. The constraining surface may be wholly encased within the substance of the jaw member, such that tissue cannot get caught between the pivotal connection and the constraining surface.

In a preferred embodiment, the constraining surface of each jaw member can be identical in shape, such that the movement of each of the pivotal connections between the two sets of corresponding connection member and articulation member corresponds with the other. In an alternative embodiment, the shape of each constraining surface may be different. However, the difference in shape must be such that, on reciprocation of the reciprocating member, movement of the jaw members relatively toward or away from one another is possible.

As defined, the pivotal connection between one connecting member and its corresponding articulation member is adapted to engage each constraining surface. In a preferred embodiment, said pivotal connection may slidably engage the constraining surface. In a further preferred embodiment, said movement may occur by rolling of the pivotal connection along the constraining surface. Indeed, providing that the pivotal connection between one connecting member and its corresponding articulation member is capable of moving along the longitudinal axis of the constraining surface, there is a multitude of possible constructions for the constraining surface which are included by this invention.

The articulating means can be positioned in such a way that although positioned substantially between the surfaces of the jaw members which face one another, it does not impact on the ability of the jaw members to move relatively away from, or relatively toward, one another.

The device may, however, be constructed such that the articulating means is located adjacent or at one side of the device, namely lateral to either one of the jaw members. In such an embodiment, four connecting pins can be utilised to mount the jaw members to the articulating means. A first pin can extend from the second pivotal connection between the first connecting member and the first articulation member to engage the constraining surface of the first jaw member. A second pin can extend from the third pivotal connection between the second connecting member and the second articulation member to engage the constraining surface of the second jaw member. A third pin can constitute the fifth pivotal connection and extend between the first articulating member to a position on the second jaw member distal its proximal end. A fourth pin can constitute the sixth pivotal connection and extend between the second articulating member to a position on the first jaw member distal its proximal end.

In an alternative embodiment, there may be two or more articulating means on one or either side of a midline of the instrument. The pivotal connection between the two articulating members would not necessarily extend across the midline in this embodiment, in order to allow for the passage of materials from the proximal end to the distal end of the jaw members, or vice versa. Such a configuration would provide bilateral stability and a central channel through which such procedures as stapling, cutting or clip applying could occur, and through which any diagnostic or therapeutic modality, biopsy device or sensing probe could be deployed. In this embodiment, the reciprocating member may be uniaxial or biaxial to allow for clips or a blade or any other therapeutic or diagnostic device to be stored or deployed in the proximal part of the instrument prior to advancement. These procedures involve a device stored within or beside the reciprocating member being advanced to a position between the jaw members from the proximal end of the device. Alternatively, catheters, blades, biopsy forceps, and suction or irrigation means can be applied to the space between the jaw members from the proximal end of the device via a lumen within or beside the reciprocating member or within or beside the lumen of the support means.

In an alternative embodiment, a plurality of devices, as described above, can be connected to one another side-by-side in the device. In such an embodiment, a plurality of pins can be used to connect the appropriate pivot means of each articulation means together, thereby ensuring that only one reciprocating member is required to control the movement of the jaw members of each device relatively away from or relatively toward one another.

The device can be considered in a closed position when the jaw members are lying flat against one another, and in an opened position when there is a space between the jaw members. The device is preferably opened when the reciprocating member is pushed relatively forward (in a direction toward the distal end of the device) and closed when the reciprocating member is pulled relatively backward (in a direction toward the proximal end of the device). In an alternative embodiment, however, variations in construction may render it possible to open the device by pulling the reciprocating member relatively backward and close it by pushing the reciprocating member relatively forward. In addition, different movements of the reciprocating member could be utilised to achieve opening and closure of the device including, for example, by rotating the reciprocating member.

By constructing the device so that the articulation means is located lateral to either one of the jaw members, as disclosed in a preferred embodiment above, or if two articulation means are located either side of the midline of the instrument, a significant advantage arises: When the articulation means is to one side or on both sides of the midline, the space between the surfaces of the jaw members which face one another will always be empty while the jaw members are relatively apart (provided, of course, that there is no tissue therebetween). Such a space creates a central channel through which other devices can be passed. Indeed, this particular construction provides access for a vast array of surgical instruments including, for example, catheters and any other means to provide suction and/or irrigation, blades and other cutting instruments, staplers, stapler/cutter combination devices, cameras, sensing probes, electrocautery, biopsy forceps or needles and devices for applying clips. In the latter application, clips could be stored within or beside a lumen of the reciprocating member or within or beside a lumen of the support means and advanced as the clips are required. Alternately, clips could be deployed within the jaw members of the instrument once the instrument is within the body cavity. The use of these embodiments of the invention are not, however, limited to circumstances in which such devices, staplers, needles, etc, are deployed via the device itself, but also include circumstances in which they are deployed into the operative field by alternative means. Having the articulation means to one side also allows side engagement of the jaw members with tissue.

Another desired feature of the invention is that the gripping surface of the jaw members remain parallel to one another throughout the full range of motion of the jaw structure, from a closed position to a fully open position. This feature renders it possible to adapt the invention for a variety of purposes and for use in a variety of ways. For example, by mounting a calibrated measuring scale onto the device, it is possible to measure the thickness of any tissue grasped between its jaw members. In prior art disclosures, where jaw members of related surgical devices open and close about a single pivot point, such a calibrated measuring scale would only be able to provide an estimate of the dimensions of tissue grasped between its jaws. This is because of the indeterminability of the exact point along the length of the jaw members where the tissue would actually be grasped. Where the jaw members remain parallel at all times, such as in the present invention, it is not important or necessary to determine at what location, along the length of the jaw members, the tissue is actually grasped in order to obtain an accurate measurement of the tissue thickness.

In addition to measuring tissue thickness, the device may also be adapted to measure the stiffness and other mechanical properties of the tissue being grasped. This may be achieved by adding strain gauges or other load measuring devices to the jaw members, articulation members and/or connecting members which would measure the load being applied to the tissue as well as the corresponding compressive displacement caused to the tissue by means of the jaw members as they close around it.

In yet a further preferred embodiment, the use of a calibrated measuring scale can provide a means for making incisions or cuts of precise dimensions. In such an embodiment, a blade of any shape can be connected to the surface of the first jaw member which faces the corresponding surface of the second jaw member; and the second jaw member can be constructed such that its said corresponding surface has a receptacle of a corresponding shape to the blade on the first jaw member, and is capable of receiving the blade when the device is closed and the surfaces of the jaw members which face one another are in contact. In addition, the calibrations on the measuring scale are adapted to correspond to calibrations on the blade. Accordingly, as the device is closed and the blade is gradually received by the receptacle, the tissue caught therebetween is cut, and the dimensions of the cut are precisely controlled by the surgeon who is able to refer to the calibrated measuring scale while advancing the reciprocating member relatively toward the fourth pivotal connection, thereby closing the device.

The feature that the jaw members move in parallel relation to one another is also of considerable benefit in circumstances where the device is being used in procedures requiring ultrasound visualisation or other imaging modalities. In preferred embodiments, wherein the device is being used in such procedures, the invention is adapted for incorporating components of the particular imaging modality equipment into its jaw members. In the case of ultrasound, for example, the emitter could be incorporated into the first jaw member, while the receiver is incorporated into the second jaw member; or alternatively, a pulse-echo ultrasound transducer/receiver could be incorporated into the first jaw member, while the second jaw member is used to secure tissue to the first. This would provide the surgeon with an ability to determine the exact location where the tissue is being grasped along the length of the jaw members. Such an ability would be of particular value in, for example, the performance of a laparoscopic cholecystectomy, where identification of the anatomical relationship between the cystic duct and surrounding vessels is crucial.

The device can further be adapted for administering radiotherapy or other forms of electromagnetic radiation or performing lithotripsy or therapeutic ultrasound. In such embodiments of the invention, the preferred parallel relation of the jaw members is also of particular value since one jaw member can act as an emitter while the other acts as a shield. This makes it possible to administer a very high concentration of radiotherapy or lithotripsy to a specified site of action, without fear of damaging surrounding tissues.

According to an alternative embodiment of the invention, the device may be controlled from a remote location, for example, by means of remote robotic actuation by a surgeon in a different location to the patient. In order to accurately determine the appropriate force to use in, for example, manipulating, grasping, cauterising, stapling, clipping, or clamping tissues from a remote location, it will be necessary to rely on feedback from pressure sensors. Surgical instruments in which jaw members open and close about a single pivot point will not provide an appropriate structure for using pressure sensors. This is due to the fact that once tissue has been grasped, a pressure differential exists along the length of the jaw members, from their point of meeting to their distal ends. In the case of the present invention, however, where the jaw members preferably remain parallel at all times, there is no pressure differential along their length and, therefore, no difficulty in incorporating pressure sensors into the design.

In embodiments of the invention where the device is being used in conjunction with a monitor to perform minimal access surgery, it may be advantageous to incorporate telemetry devices within the jaw members, so that the position of the instrument in space can be determined. This may be correlated with diagnostic information supplied by probes at the tip and conveyed to the surgeon either directly, or through a display on the monitor, indicating the precise location of the diagnostic data.

In embodiments of the invention wherein the device is being used as a delivery means, capable of delivering, further devices, such as, implants, grafts or stents, to a desired location in the body of a patient, the feature that the jaw members move in parallel relation to one another is particularly advantageous as it allows for different mechanisms to carry such devices. For example, in the case of delivering a graft or stent to the lumen of a vessel in the body of a patient, it may be desirable that the graft or stent be in a radially compressed state before being deployed from the delivery means. In such cases, the graft or stent may initially be compressed to a radially compressed state between the jaw members, and allowed to spring out to a radially expanded state upon release from the grip of the jaw members. Alternatively, where such a graft or stent is manufactured such that it is initially in a radially compressed state and may be expanded to a radially expanded state by physical dilatation, then prior to delivery of the graft or stent, the jaw members of the device should be in a closed position whereby they can be inserted into the lumen of the graft or stent. Once such graft or stent has been delivered to the desired location, the jaw members of the device may be opened, thereby causing the graft or stent to be expanded to a radially expanded state. Such an embodiment may also involve the stent being loaded onto the jaw members which are in an open state. The stent would therefore be deployed by closing the jaw members, once the stent was firmly in place, leaving it behind as the device is removed from within it. In all these embodiments for endo-luminal applications, blood and fluid are able to flow freely through the lumen of the device whilst it is being used. This is especially important where the device is being used to compress material in the wall of the vessel, as occurs during angioplasty.

In yet a further preferred embodiment, a compliant extension member having a longitudinal axis, a distal end and a tip, extends from each of the distal ends of the jaw members. Such compliant extension members can provide the device with the ability to substantially replicate forceps and, therefore, render it capable of grasping small amounts of tissue in a precise manner at the distal extremity of the instrument. In such embodiments, the compliant extension members are generally of a material and construction which causes their distal ends to have a tendency to bend away from their longitudinal axis and towards each other. In addition, the orientation for each compliant member, when extending from the distal end of each jaw member, is such that when the respective distal ends of the compliant members are bent, their tips can come into contact with one another. In other words, when the device is maximally open, and the jaw members maximally apart, although the distal ends of the compliant extension members are bent, their tips may still have a space between them. However, as the jaw members are caused to move relatively toward one another, the tips of the compliant extension members will gradually get closer until such time as they come into contact.

On moving the jaw members relatively toward one another beyond the point at which the tips of the compliant members are in contact, causes the distal ends of the respective compliant members to gradually flex into line with their longitudinal axes, and does not prevent the device from closing. Indeed, when the jaw members lie flat against one another, the compliant extension members also preferably lie flat against one another.

The components of the device may be formed of an appropriate solid surgical material including stainless steel, atraumatic plastic, or one of various alloys. In alternative embodiments, however, the device may be manufactured such that each component is made up of a different material to the others.

A further advantage of the present invention arises when the instrument is to be used for clamping an artery during arteriotomy. In this case, the pulsatile pressure of the blood against the jaw members of the instrument can create further problems, which may not be adequately overcome with conventional patterns of conventionally shaped teeth. If the grip is inadequate, each pulsatile push of blood may cause the instrument to move toward the arteriotomy site. This is known as "marching", and causes the length of artery with which the surgeon can work to progressively decrease, and the risk of the clamp falling off the end of the arteriotomy site (resulting in potentially substantial blood loss) to considerably increase. The construction of the present device ensures that sufficient grip can be applied to an artery to prevent marching while at the same time minimising the chance of trauma to the artery.

The construction of the present device enables it to incorporate various diagnostic, therapeutic and mechanical property testing modalities that maximises its utility. In addition, it is useful to correlate any diagnostic information with what the surgeon sees on the monitor during the procedure to give an enhanced "virtual" perspective of the operative field.

In a further aspect, the present invention consists in a device for manipulating tissues in the body of a patient, the device including:

a support means;

a reciprocating member which moves relative to the support means; and an articulated jaw.structure having at least two jaw members and an articulating means, the jaw members each having a proximal end, a constraining surface adjacent the proximal end and a rotating-pivot means distal the proximal end, and the articulating means having at least two connecting members and at least two articulation members, the connecting members and the articulation members being pivotally attached to one another in a configuration which can be changed from a first to at least a second orientation by relative movement of the reciprocating member, wherein when in the first orientation, corresponding points on each of the jaw members are separated by a first distance, and when in the second orientation, corresponding points on each of the jaw members are separated by a second different distance.

BRIEF DESCRIPTION OF THE DRAWINGS

By way of example, preferred embodiments of the invention are described with reference to the accompanying drawings, in which:

FIG. 1a is an exploded perspective view of one embodiment of the device according to the present invention;

FIG. 1b is a perspective view of the assembled device of FIG. 1a;

FIG. 1c is a schematic view of the assembled device of FIG. 1a;

FIG. 1d is a plan view of the device of FIG. 1a;

FIG. 2b is a perspective view of the assembled device of FIG. 2a;

FIG. 2c is a schematic view of the assembled device of FIG. 2a;

FIG. 2d is a plan view of the device of FIG. 2a;

FIG. 2e is a side elevational view of the device of FIG. 2a depicted with the jaw members in an opened position;

FIG. 2f is an end elevational view of the device depicted in FIG. 2e;

FIG. 2g is a side elevational view of the device of FIG. 2a depicted with the jaw members in a closed position;

FIG. 2h is an end elevational view of the device depicted in FIG. 2g;

FIG. 3b is a perspective view of the assembled device of FIG. 3a;

FIG. 3c is a schematic view of the assembled device of FIG. 3a;

FIG. 3d is a plan view of the device of FIG. 3a;

FIG. 3f is an end elevational view of the device depicted in FIG. 3e;

FIG. 3g is a side elevational view of the device of FIG. 3a depicted with the jaw members in a closed position;

FIG. 3h is an end elevational view of the device depicted in FIG. 3g;

FIG. 5a is a cross-sectional view of an embodiment of the invention in which a compliant extension member extends from the distal end of each jaw member and the device is closed with the jaw members lying flat against one another (for reasons of clarity, the articulation means and reciprocating member are not shown in this Figure);

FIG. 5b is a further cross-sectional view of the device of FIG. 5a wherein the device is in an open position and the jaw members are relatively apart from one another.

PREFERRED MODE FOR CARRYING OUT
THE INVENTION

Figure 6:
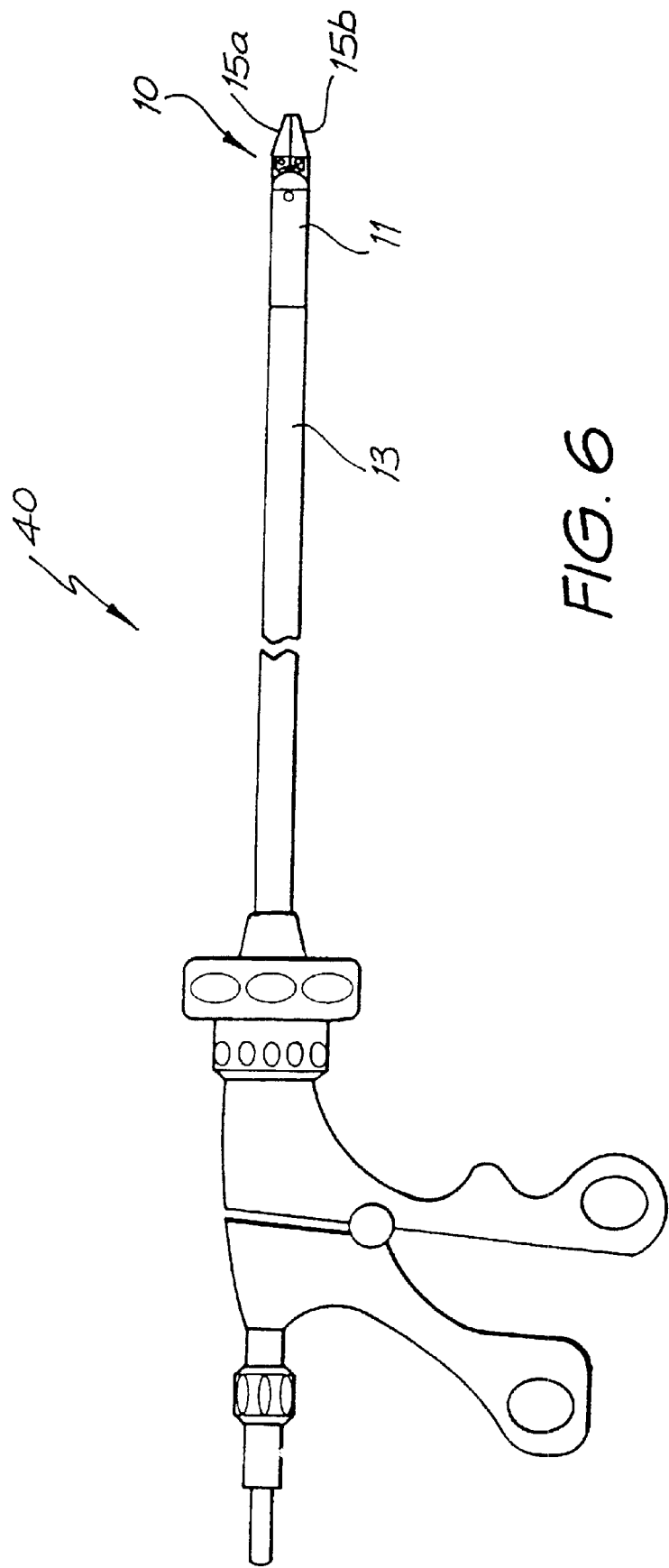
FIG. 6 is a side elevational view of an embodiment of the device adapted for use with, and incorporated into, a conventional laparoscopic grasper.

One embodiment of a surgical instrument according to the present invention is depicted generally as 10 in FIGS. 1a to 1h. The instrument 10 is adapted for incorporation into a minimally invasive grasper 40 as illustrated in FIG. 6. It will, however, be appreciated that the instrument 10 can be incorporated into devices other than the depicted minimally invasive grasper 40.

The instrument 10 includes a support 11, an articulated jaw structure 12, and a reciprocating rod 14. The articulated jaw structure 12 comprises firstly a first jaw member 15a and a second jaw member 15b. The jaw structure 12 also includes two connecting members 24a,24b, and two articulation members 25a,25b. Both the proximal end of the first connecting member 24a and the proximal end of the second connecting member 24b are pivotally attached by common pivot pin 26 to the distal end of the reciprocating member 14. The first and second connecting members 24a,24b respectively extend to distal ends that are pivotally attached to respective proximal ends of the first and second articulation members 25a,25b. A pivot pin 27a connects the first connection member 24a and the first articulation member 25a. The pivot pin 27a is also adapted to engage the constraining surface 18a of the first jaw member 15a. Similarly, a pivot pin 27b connects the second connection member 24b and the second articulation member 25b and is adapted to engage the constraining surface 18b of the second jaw member 15b. The first and second articulation members 25a,25b each respectively extend to distal ends that are pivotally attached to respective pivot pins 19b,19a mounted to the second and first jaw members 15b,15a, respectively. The first and second articulation members 25a,25b are pivotally attached where they cross one another by pin 28 mounted to the support 11.

As the reciprocating rod 14 is pivotally attached by common pivot pin 26 with the first and second connecting members 24a,24b, it can be moved relatively forward (in a direction toward the distal end of the device 10) and relatively backward (in a direction toward the proximal end of the device 10), in the same plane as the device 10. Such movement of the reciprocating rod 14 leads to the articulated jaw structure 12 changing configuration in a concertina fashion from a first to at least a second orientation. In the depicted instrument 10, when the reciprocating rod 14 is pushed relatively forward, the jaw members 15a,15b are caused to move apart, thereby opening the jaw members 15a,15b of the instrument 10. When the reciprocating rod 14 is pulled relatively backward, the jaw members 15a,15b are caused to move towards each other, thereby closing the jaw members of the device 10.

In the instrument 10, the support 11 is cylindrical with a lumen 70, a proximal end 72, and a distal end 74. In the depicted embodiment, the support 11 is mountable to a cylindrical extender 13 that also has a lumen 70. In the depicted embodiment, the distal ends of the jaw members 15a,15b extend distally beyond the distal end 74 of the support 11. It will be appreciated that in other embodiments, the support 11 could extend beyond the distal ends of the jaw members 15a,15b. Such an extension of the support 11 can act as a tissue guard and help prevent tissue entering the region between the jaw members 15a,15b and being damaged by the articulation members 25a,25b on movement of the jaw members 15a,15b.

While the depicted support 11 has a substantially constant cross-sectional diameter, the diameter could vary along its length. For example, the diameter of the support means 11 could gradually taper from a larger cross-sectional diameter at its proximal end 72 to a smaller cross-sectional diameter at its distal end 74. In an alternative embodiment, the reverse may be the case. The tapering of the cross-sectional diameter may occur at any point along the length of the support 11. The tapering may be gradual or may occur very rapidly. In another embodiment, the diameter may not taper and instead may change from one size to another, thereby forming a circumferential step in the support 11.

Each of the jaw members 15a,15b have respective smoothly curved surfaces 17a,17b and respective orifices 19c,19d distal their proximal ends. The orifices 19c,19d are adapted to receive pivot pins 19a,19b, respectively to allow pivotal connection of articulating members 25b,25a to the jaw members 15a,15b, respectively.

In cases where the instrument 10 is to be used for clamping body tissue, such as a blood vessel, the jaw members 15a,15b can be said to have clamping surfaces 21a,21b, respectively. These clamping surfaces may, if necessary, be lined with a plurality of gripping members. Such gripping members may comprise several rows of teeth and could include cross-hatched rows of teeth.

In the embodiment of the instrument depicted generally as 10, the connecting members 24a,24b and articulating members 25a,25b are mounted along one side of the jaw members 15a,15b. It will be appreciated that the instrument 10 could be constructed such that the connecting members 24a,24b and articulating members 25a,25b are mounted to the other side of the jaw members 15a,15b to that depicted in FIGS. 1a–1h.

By constructing the device 10 so that the articulation means 16 is located lateral to the jaw members 15a,15b, a significant advantage arises: when the articulation means 16 is to one side, the volume between the clamping surfaces 21a,21b while the jaw members 15a and 15b are apart (provided, of course, that there is no tissue therebetween) is left empty. Such a space creates a central channel 80 through which other instruments can be passed through the instrument 10.

The construction of the articulated jaw structure 12 is such that the clamping surfaces 21a,21b of the jaw members 15a,15b remain parallel to one another throughout the full range of motion of the jaw members, from a closed position to a fully open position. This feature of the instrument 10 renders it possible to adapt the instrument for a variety of purposes and for use in a variety of ways beyond its depicted use as grasper.

For example, by mounting a calibrated measuring scale onto the instrument 10, it is possible to measure the thickness of any tissues grasped between the jaw members 15a,15b. In prior art disclosures, where jaw members of scissor-action surgical devices open and close about a single pivot point, such a calibrated measuring scale would only be able to provide an estimate (at very best) of the size of tissue grasped between its jaws. This is because of the indeterminability of the exact point along the length of the jaw members where the tissue would actually be grasped. In the present invention, it is not important to determine at what location, along the length of the jaw members 15a,15b, the tissue is actually grasped in order to obtain an accurate measurement of the tissue thickness.

In addition to measuring tissue thickness, the instrument 10 can be adapted to measure the stiffness and/or other mechanical properties of the tissue being grasped. This may be achieved by adding strain gauges to the jaw members 15a,15b, articulation members 25a,25b and/or connecting members 24a,24b to measure the load being applied to the tissue as well as the corresponding compressive displacement caused to the tissue by means of the jaw members 15a,15b as they close around the tissue.

Figure 1B:
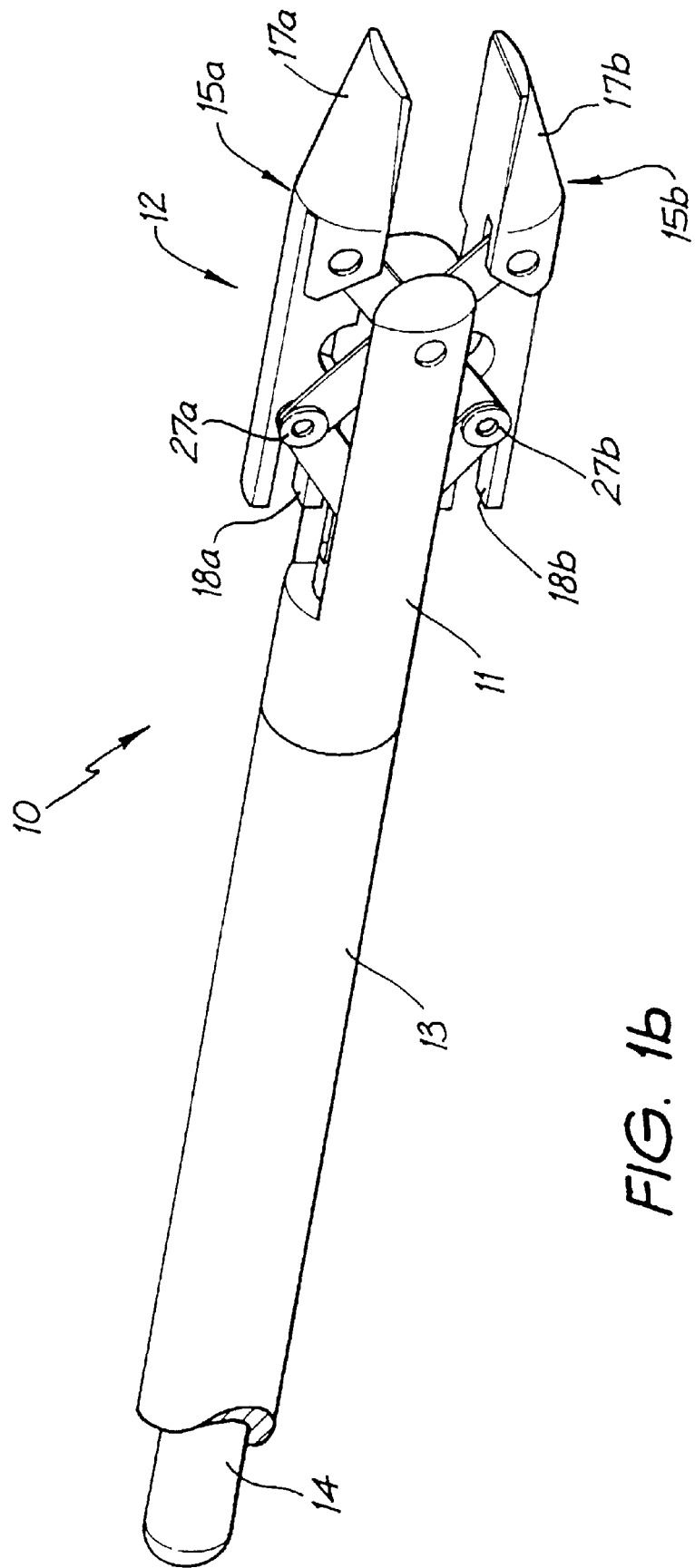
Figure 1C:
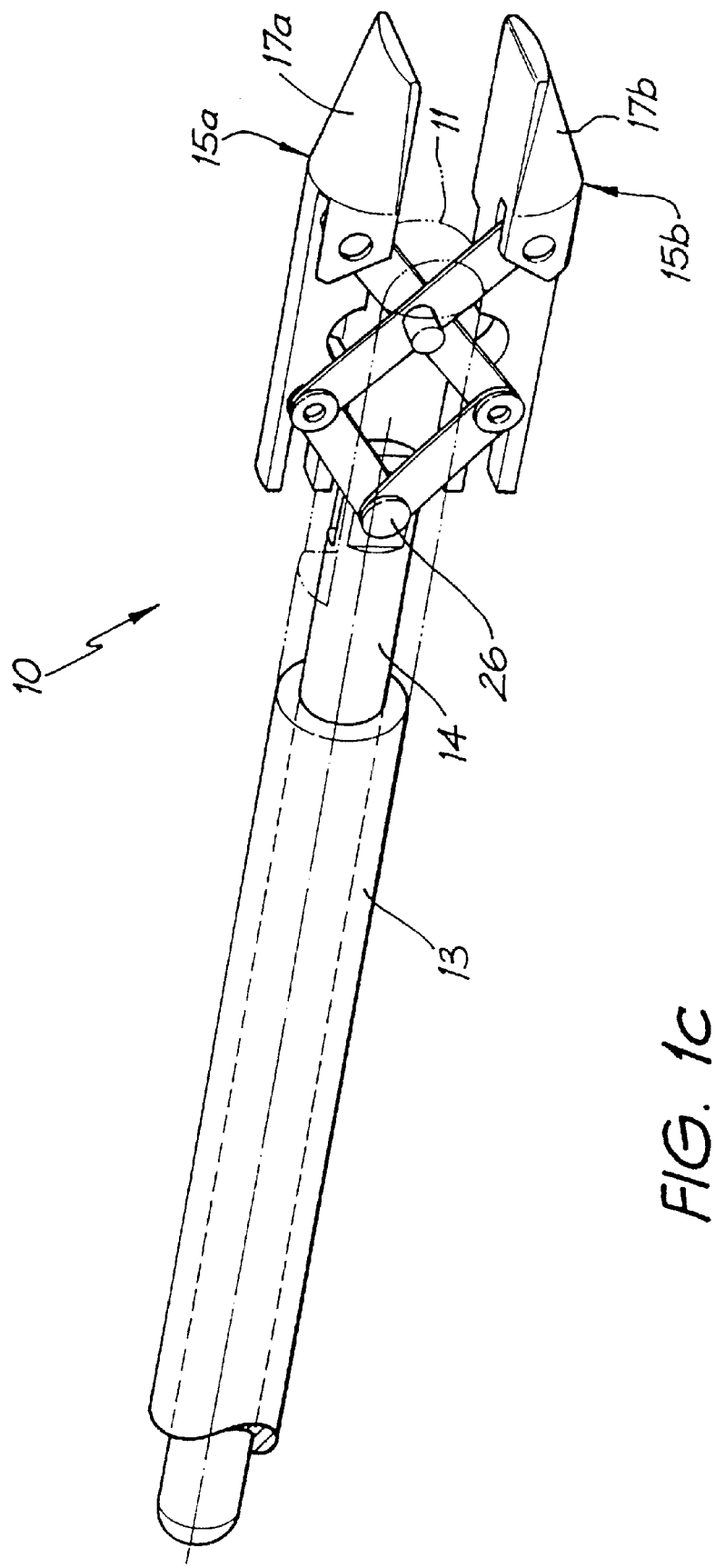
Figure 1D:
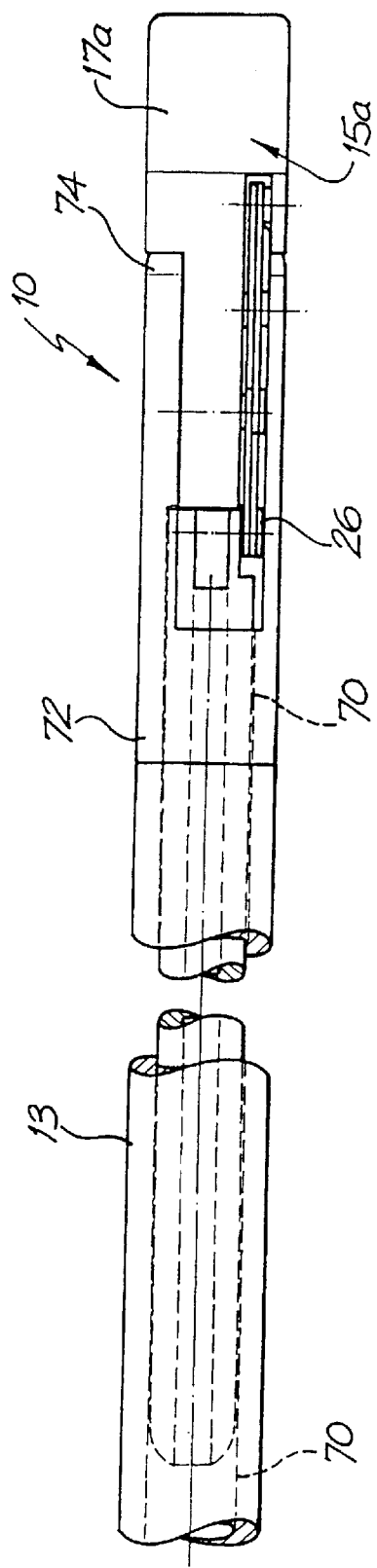
Figure 1E:
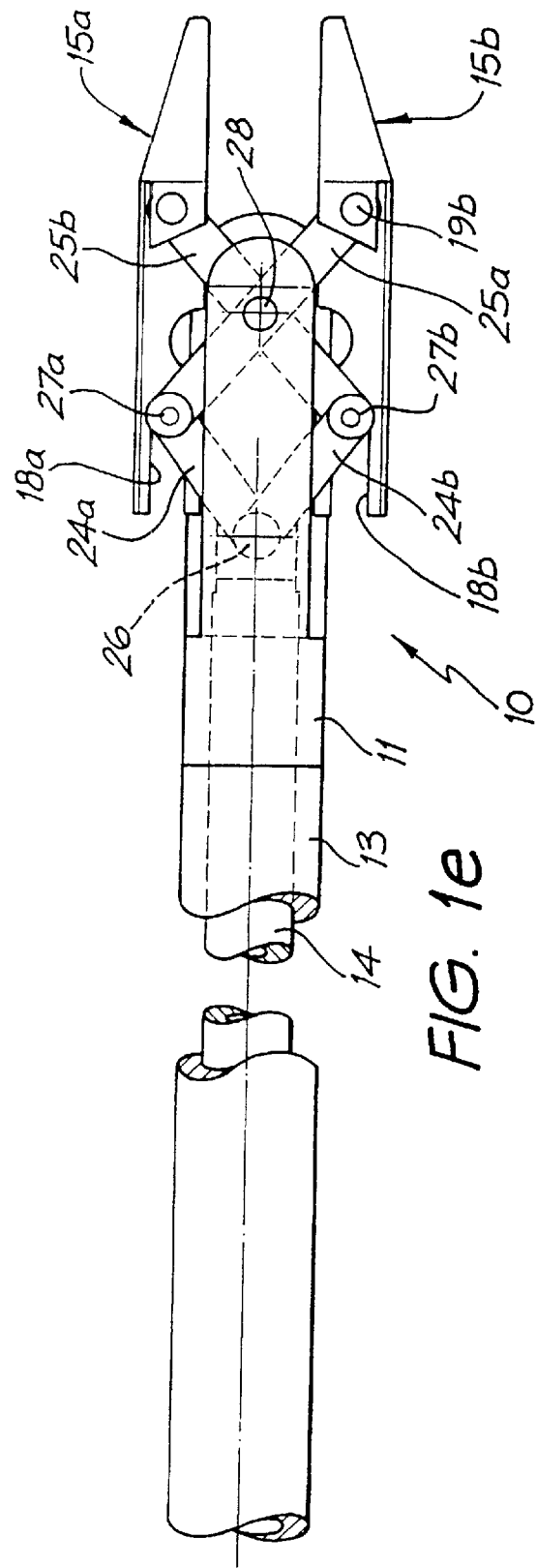
FIG. 1e is a side elevational view of the device of FIG. 1a depicted with the jaw members in an opened position.
Figure 1G:
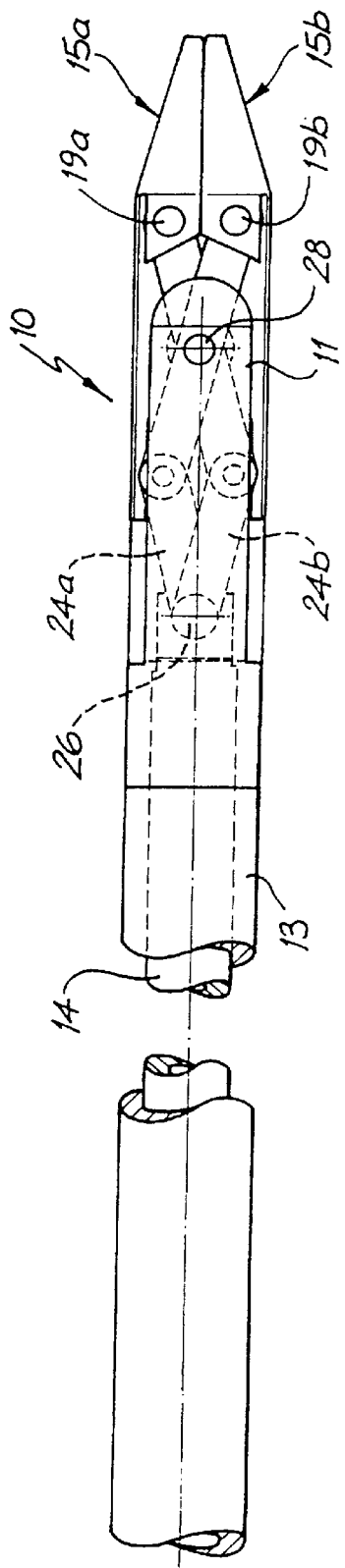
FIG. 1g is a side elevational view of the device of FIG. 1a depicted with the jaw members in a closed position.
Figure 1H:
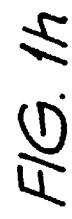
FIG. 1h is an end elevational view of the device depicted in FIG. 1g.
Figure 1F:
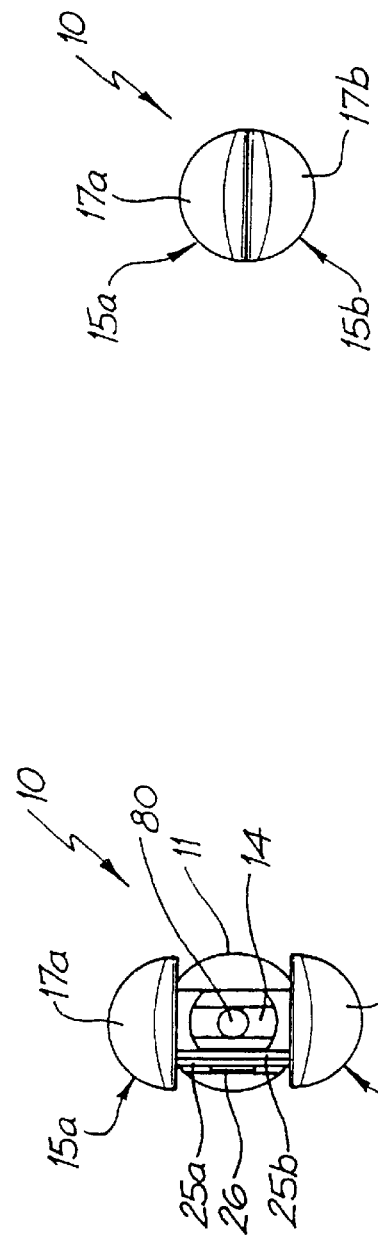
FIG. 1f is an end elevational view of the device depicted in FIG. 1e.
Figure 2A:
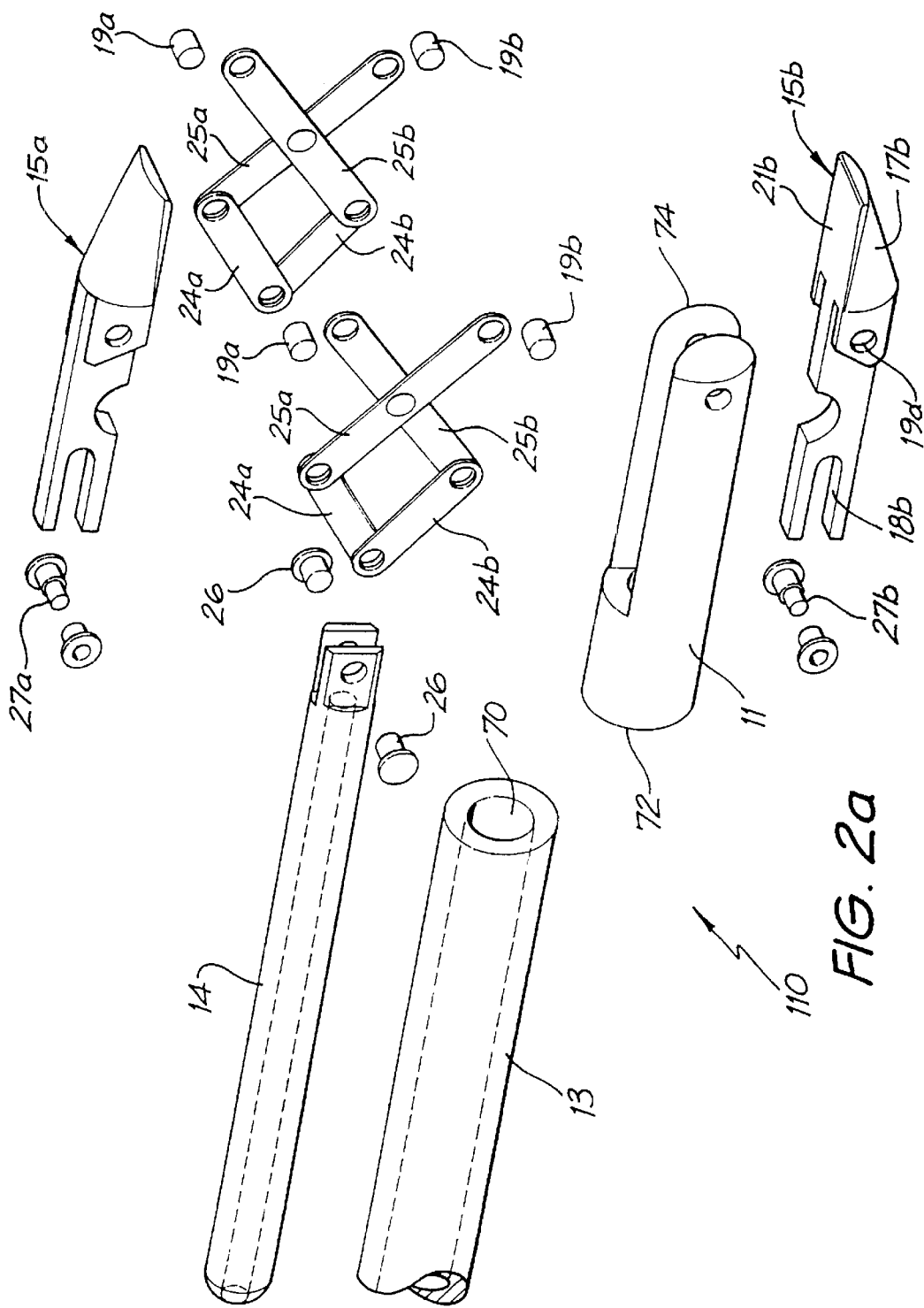
FIG. 2a is an exploded perspective view of a second embodiment of the device according to the present invention.
Figure 2B:
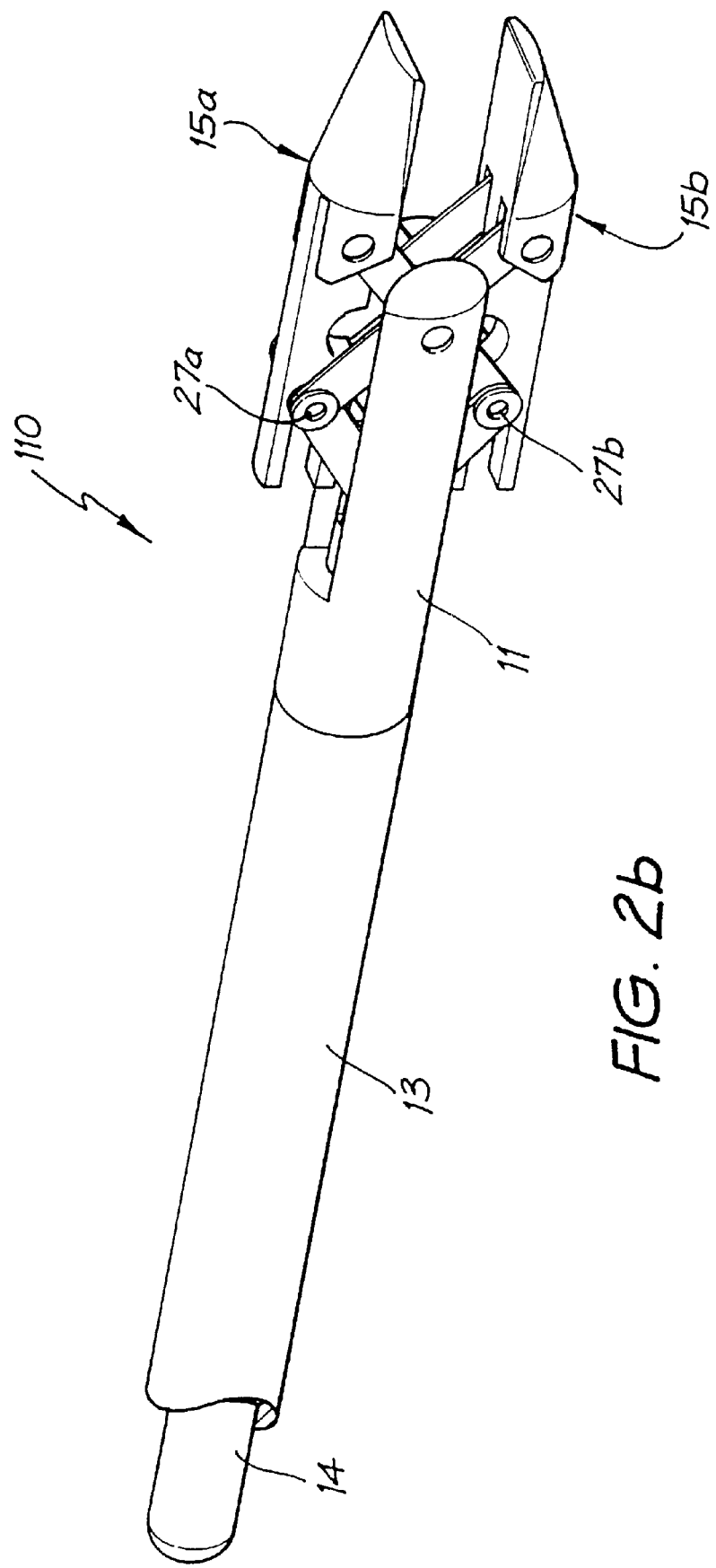
Figure 3A:
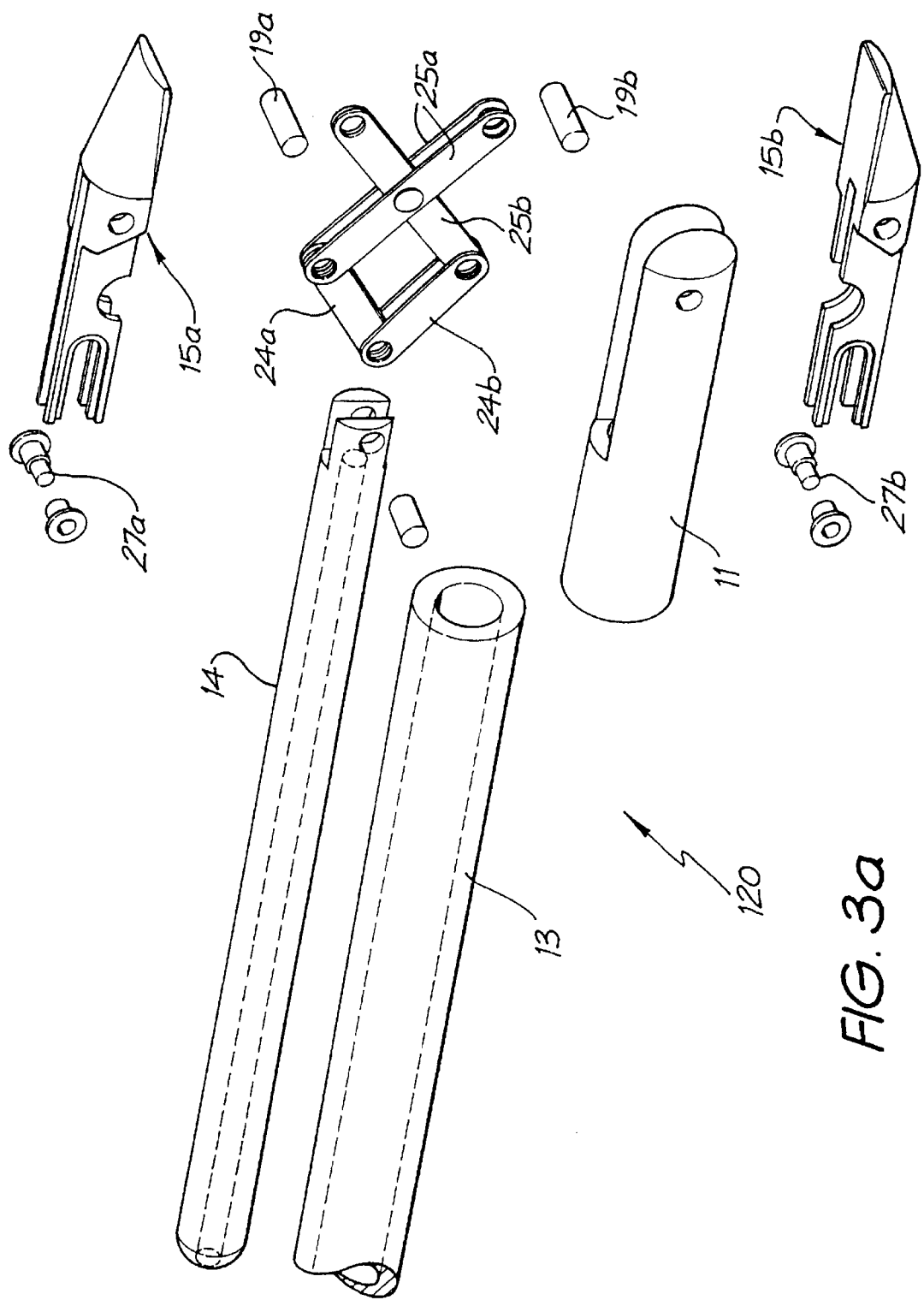
FIG. 3a is an exploded perspective view of a third embodiment of the device according to the present invention.
Figure 3B:
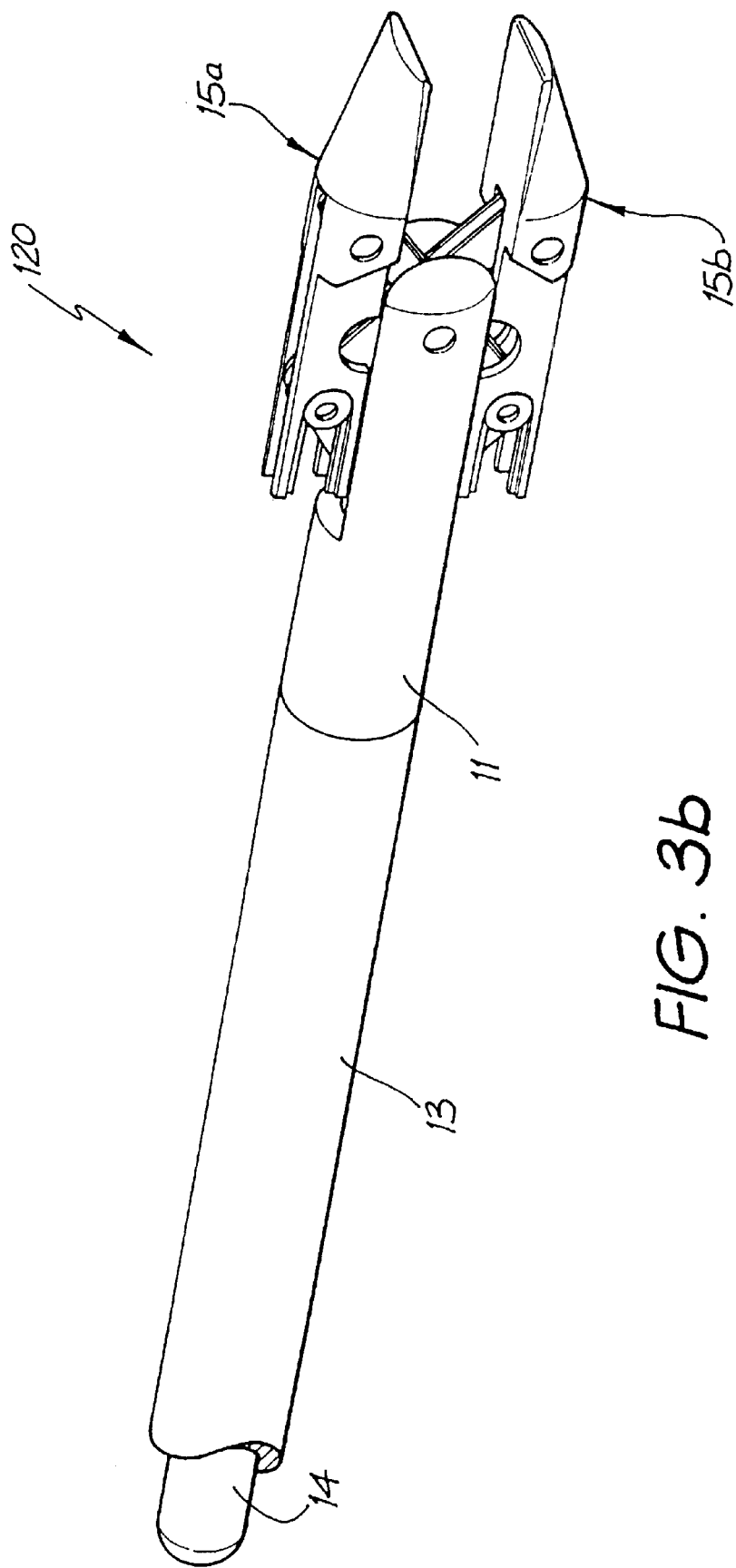
Figure 3C:
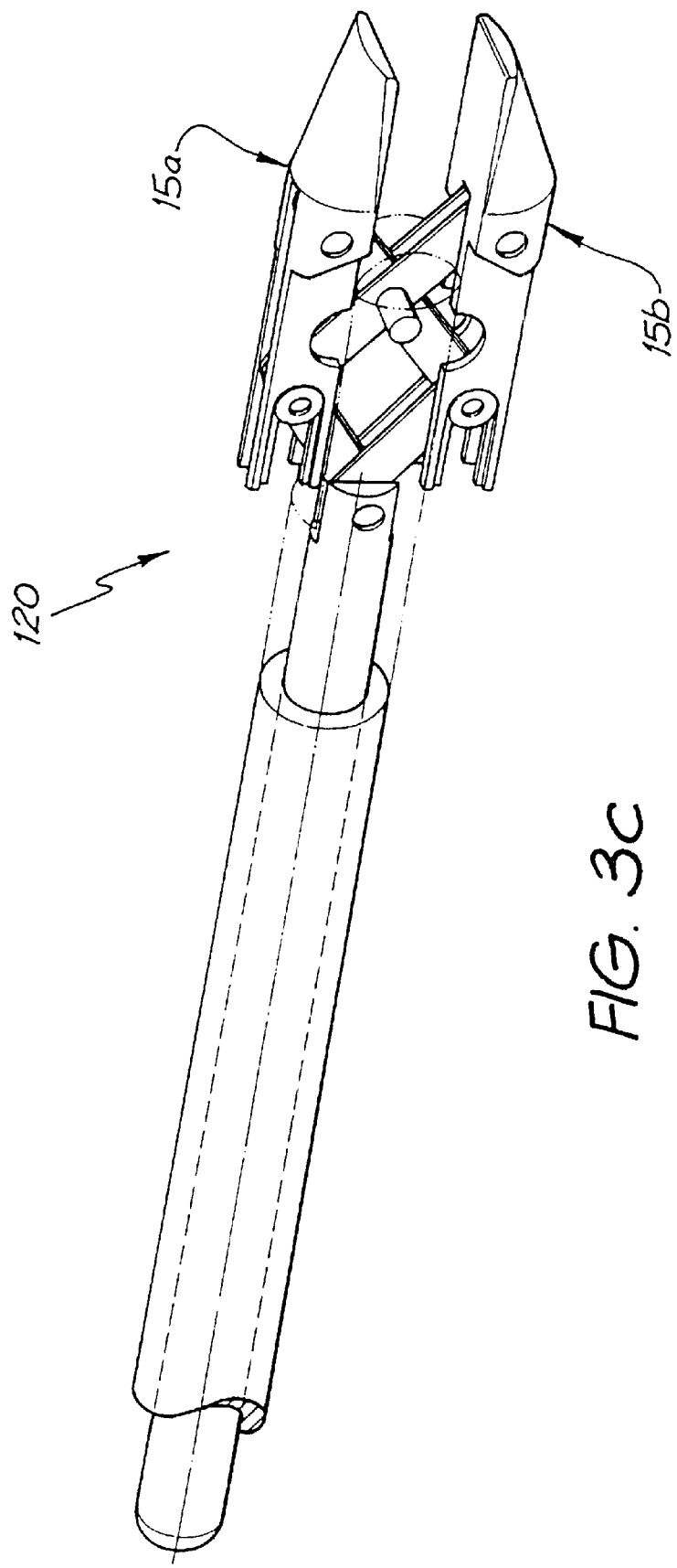
Figure 3D:
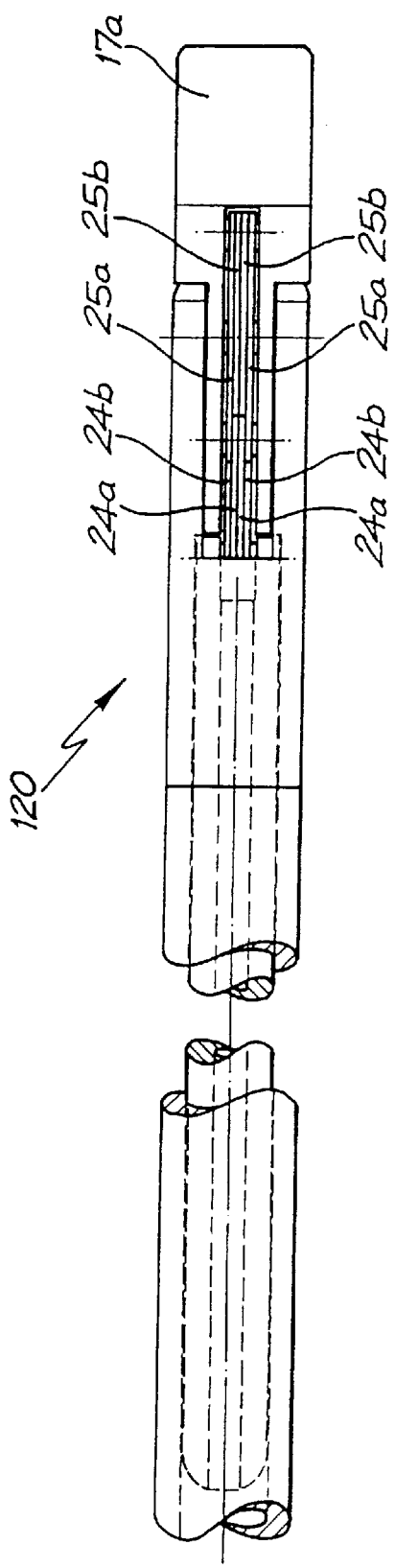
Figure 3E:
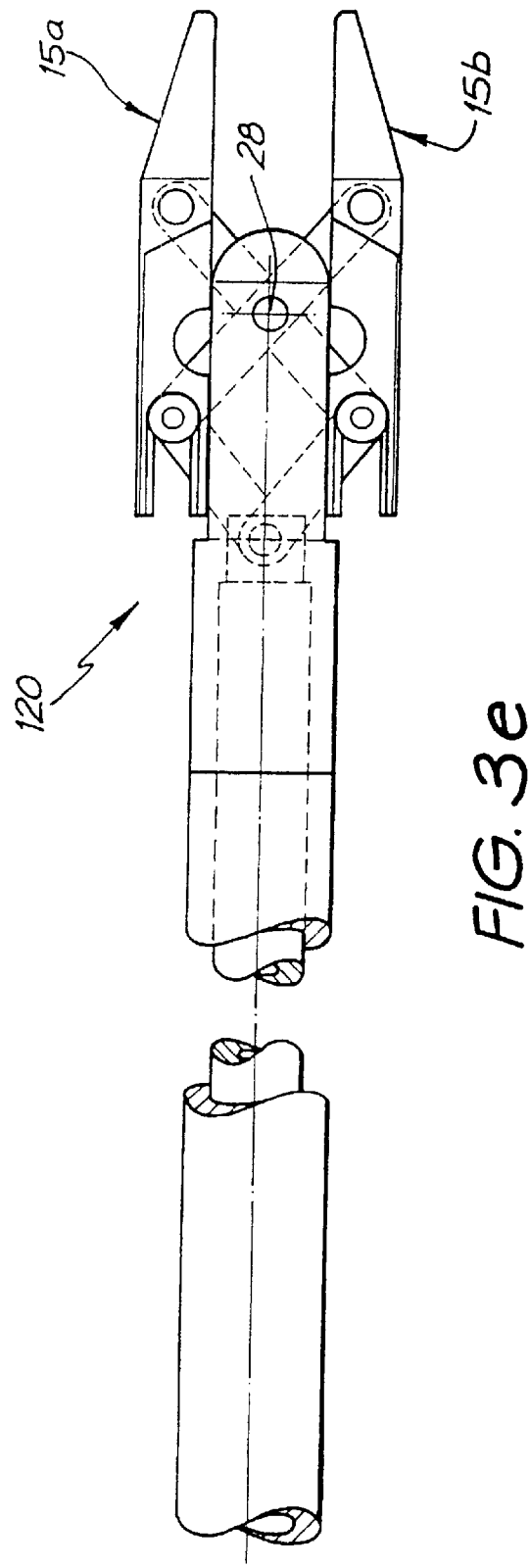
FIG. 3e is a side elevational view of the device of FIG. 3a depicted with the jaw members in an opened position.
Figure 4:
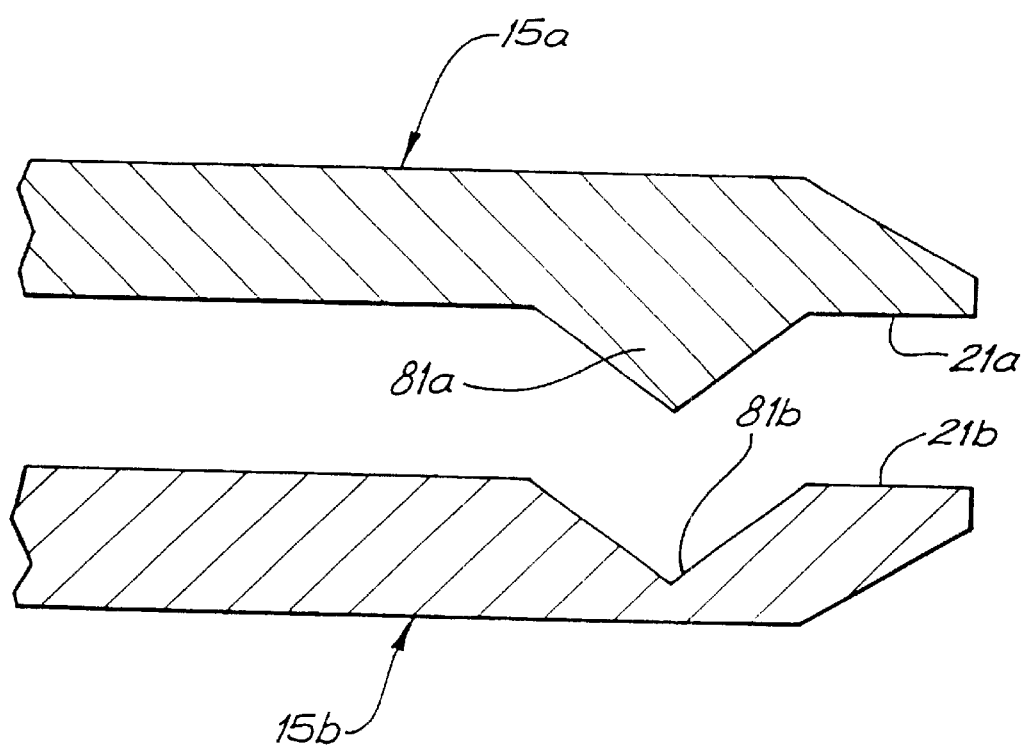
FIG. 4 is a cross-sectional view of the jaw members of another embodiment in which the device is to be used as a cutter (for reasons of clarity, the articulation means and reciprocating member are not shown in this Figure)

In yet further preferred embodiments, the use of a calibrated measuring scale can provide a means for making incisions or cuts of precise dimensions. In one embodiment, a blade 81a of appropriate shape can be connected to the surface 21a of the first jaw member 15a, and the second jaw member 15b can be constructed such that its said corresponding surface 21b has a receptacle 81b of a corresponding shape to the blade 81a and is capable of receiving the blade 81a when the instrument 10 is closed (see FIG. 4). In addition, the calibrations on the measuring scale can be adapted to correspond to calibrations on the blade 81a. Accordingly, as the jaw members 15a,15b are closed and the blade 81a is gradually received by the receptacle 81b, the tissue caught therebetween is cut, and the dimensions of the cut are precisely controlled by the surgeon who is able to refer to the calibrated measuring scale while advancing the reciprocating member 14 relatively toward the pivot pin 28 mounted to support 11, thereby closing the instrument 10.

That the jaw members 15a,15b move in parallel relation to one another is of considerable benefit in circumstances where the instrument 10 is being used in procedures requiring ultrasound visualisation or other imaging modalities. In such cases, the instrument 10 is modified to incorporate components of the particular imaging modality equipment into each of its jaw members 15a,15b. When using ultrasound with the instrument 10, for example, the emitter could be incorporated into the first jaw member 15a, while the receiver is incorporated into the second jaw member 15b, so that the active surfaces of both the emitter and receiver face the same direction as the clamping surfaces 21a,21b respectively of their corresponding jaw members 15a,15b. This would provide the surgeon with, for example, an ability to determine the exact location where the tissue is being grasped along the length of the jaw members 15a,15b.

The instrument 10 can similarly be adapted for administering radiotherapy or performing lithotripsy with high dose concentrations, where an emitter is incorporated into the first jaw member 15a, while a shield is incorporated into the second jaw member 15b.

As depicted in FIGS. 5a and 5b, compliant extension members 90a,90b having respective distal tips 91a,91b, extend from each of the distal ends of the jaw members 15a and 15b. The compliant extension members 90a,90b provide the instrument 10 with the ability to substantially replicate the action of forceps and, therefore, render it capable of grasping small amounts of tissue in a precise manner. The compliant extension members 90a,90b are generally of a material and construction which causes their distal tips 91a,91b respectively to have a tendency to bend away from their respective longitudinal axes and towards each other. When the instrument 10 is open to its maximum extent, the tips 92a,92b will normally still have a space therebetween. However, as the jaw members 15a,15b are caused to move relatively toward one another, the tips 92a,92b gradually get closer to each other until such time as they come into contact. As the jaw members 15a,15b move relatively toward one another beyond the point at which the tips 92a,92b are in contact, the compliant members 90a,90b gradually flex and straighten as depicted in FIG. 5a.

The instrument 10 can also be adapted such that it can be controlled from a remote location. In this case, the clamping surfaces 21a,21b can be lined with pressure sensors. Such sensors would provide a surgeon, that is at a remote location from the patient, with immediate electronic feedback on the amount of pressure a remotely controlled robot is applying to the tissue being manipulated, grasped or clamped by the instrument 10.

An alternative construction of an instrument according to the present invention is depicted generally as 110 in FIGS. 2a to 2h, Those features of instrument 110 that correspond to those of instrument 10 have been identically numbered. In instrument 110, the articulated jaw structure 12 comprises two sets of connecting members 24a,24b and articulating members 25a,25b, with one set disposed on each side of the jaw members 15a,15b. In this instrument, pivot pins 26, 27a, 27b, 28, 19a and 19b are modified from those utilised in instrument 10 such that the respective pins each are connected to the two sets of connecting members and articulating members.

The articulated jaw structure 12 of instrument 110 ensures a more even application of gripping pressure to tissue clamped between the jaw members 15a,15b. The instrument 110 can also be utilised in situation where a more robust instrument is required, such as where the device is being used to manipulate or crush bone or bone fragments.

Another alternative construction of an instrument according to the present invention is depicted generally as 120 in FIGS. 3a to 3h. Those features of instrument 120 that correspond to those of instrument 10 have been identically numbered. In instrument 120, the articulated jaw structure 12 comprises a set of connecting members 24a,24b and articulating members 25a,25b that are adapted to be housed within the jaw members 15a,15b. The position of the articulated structure 12 provides even control of the range of motion of the jaw members 15a,15b on reciprocation of rod 14. This position is useful if the instrument 120 is to be used as a grasper or clamp. The positioning of the articulated structure 12 does, however, occupy the volume between the jaw members 15a,15b that can be utilised when using instruments 10 and 110 by other devices, such as catheters, cameras and the like.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for manipulating tissues of a body of a patient or animal, the device including:
   a support means;
   a reciprocating member which moves relative to the support means;
   an articulated jaw structure having:
      a first and at least a second jaw member, each jaw member having a proximal end and a constraining surface adjacent its proximal end; and
      an articulating means for articulating the jaw members in response to reciprocation of the reciprocating member, the articulating means including:
         first and second connecting members, and at least first and second articulation members, wherein the first and second connecting members are each connected by a first pivotal connection to the reciprocating member and extend to respective second and third pivotal connections, and the first and second articulation members are connected together intermediate their respective ends by a fourth pivotal connection mounted to the support means, the first articulation member extending from said second pivotal connection to a fifth pivotal connection with the second jaw member distal its proximal end, and the second articulation member extending from said third pivotal connection to a sixth pivotal connection with the first jaw member distal its proximal end, the second pivotal connection being adapted to engage the constraining surface of the first jaw member and the third pivotal connection being adapted to engage the constraining surface of the second jaw member, such that on relative movement of the reciprocating member towards or away from the fourth pivotal connection, the second and third pivotal connections are also caused to move relatively away from or towards one another, so moving the jaw members relatively away from or towards one another.

2. The device of claim 1 wherein reciprocation of the reciprocating member results in relative movement of the jaw members in parallel relation to one another throughout the range of motion of the jaw members.

3. The device of claim 2 wherein on reciprocation of the reciprocating member both jaw members each move an equal distance away from or towards each other depending on the direction of movement of the reciprocating member.

4. The device of claim 2 wherein on reciprocation of the reciprocating member one jaw member remains stationary while the other jaw member moves relative to it.

5. The device of claim 4 wherein said stationary jaw member is connected to or an integral part of the support means.

6. The device of claim 1 wherein opposed faces of the respective jaw members are planar.

7. The device of claim 6 wherein the opposed faces remain parallel throughout the range of motion of the jaw members.

8. The device of claim 1 wherein the opposed faces of the respective jaw members maintain an angular relationship with respect to one another, irrespective of the relative position of the jaw members to one another, on reciprocation of the reciprocating member.

9. The device of claim 1 wherein the relative orientation of the jaw members to each other is adjustable.

10. The device of claim 1 wherein the jaw members are moved relatively apart when the reciprocating member is pushed relatively forward in a direction toward the distal end of the device and moved relatively closer together when the reciprocating member is pulled relatively backward in a direction toward the proximal end of the device.

11. The device of claim 1 wherein the support means comprises a cylinder with a lumen having a proximal end and a distal end, the articulation means and jaw members being at least partially disposed in the lumen.

12. The device of claim 11 wherein the articulation means is secured to the support means by a pin passing through said fourth pivotal connection of the first and second articulation members.

13. The device of claim 12 wherein the fourth pivotal connection between the first and second articulation members is proximate the distal end of the support means.

14. The device of claim 11 wherein the cross-sectional diameter of the support means varies along its length.

15. The device of claim 14 wherein the cross-sectional diameter of the support means tapers from a larger cross-sectional diameter at a region adjacent its proximal end to a smaller cross-sectional diameter at a region adjacent its distal end.

16. The device of claim 11 wherein the support means extends distally from its connection with the articulating means, this extension of the support means acting as a tissue guard to prevent tissue entering the region between the jaw members and being damaged by the articulation members on movement of the jaw members.

17. The device of claim 1 wherein each constraining surface is located adjacent the proximal end of its respective jaw member.

18. The device of claim 17 wherein each constraining surface constitutes a slot which, when the device is viewed in side elevation, has a longitudinal axis and two ends.

19. The device of claim 18 wherein the slot is substantially rectangular to provide for longitudinal movement of the pivotal connection between the connection member and articulation member engaged in that slot.

20. The device of claim 1 wherein the constraining surface of each jaw member is identical in shape, such that the movement of each of the pivotal connections between the two sets of corresponding connection member and articulation member corresponds with the other.

21. The device of claim 1 wherein said second and third pivotal connections slidably engage their respective constraining surfaces.

22. The device of claim 1 wherein the articulating means is located lateral to the jaw members, with a first pin extending from the second pivotal connection between the first connecting member and the first articulation member to engage the constraining surface of the first jaw member, a second pin extending from the third pivotal connection between the second connecting member and the second articulation member to engage the constraining surface of the second jaw member, a third pin constituting the fifth pivotal connection and extending between the first articulating member to a position on the second jaw member distal its proximal end, and a fourth pin constitute the sixth pivotal connection and extending between the second articulating member to a position on the first jaw member distal its proximal end.

23. The device of claim 22 wherein an articulating means is positioned on each side of the jaw members.

24. The device of claim 1 wherein an outer surface of each jaw member has a radius of curvature to minimise tissue trauma.

25. The device of claim 6 wherein the opposed surfaces of the jaw members have a radius of curvature to minimise tissue trauma.

26. The device of claim 24 wherein the curved surface constitutes a portion of a spherical surface, an oblate spherical surface, a cylindrical surface, or a parabolic surface.

27. The device of claim 6 wherein, when the device is to be used for grasping or clamping tissues, at least a portion of the opposed surfaces of each jaw member are lined with a plurality of gripping members.

28. The device of claim 6 wherein at least one of the jaw members has a chamber, an opening in the chamber at the proximal end and a plurality of orifices on the opposed surface of the jaw member such that the space between the jaw members, the chamber and the opening at the proximal end of the jaw member are in fluid communication with one another.

29. The device of claim 28 wherein the device can include a suction means adapted to apply suction to the chamber opening and so the chamber and the plurality of orifices, such that tissue manipulated by the device is held to the opposed face while ever suction is applied to the opening.

30. The device of claim 28 wherein a pipe extends from the chamber opening to the suction means.

31. The device of claim 29 wherein the suction means is adjustable to control the amount of suction applied to the tissue manipulated by the device.

32. The device of claim 28 wherein a fluid can be passed through the chamber and the plurality of orifices of the opposed face.

33. The device of claim 32 wherein the fluid is an irrigating fluid.

34. The device of claim 1 wherein the device is mountable to a delivery means for delivery into a patient's body through an access port.

35. The device of claim 34 wherein the device is releasably mounted to the delivery means such that it can be released and left in situ to provide ongoing mechanical retraction or support.

36. The device of claim 1 wherein a lumen extends through the device from its proximal end to its distal end.

37. The device of claim 36 wherein instruments that can be passed through the lumen are selected from the group comprising a camera, diagnostic probes, suction and irrigation means, biopsy forceps, biopsy needles or any other delivery means of diagnostic or therapeutic modalities.

38. The device of claim 1 when used for manipulating, grasping, cutting, cauterising, clipping, spreading, retracting, stapling or clamping tissues during open or minimally invasive surgical procedures.

39. The device of claim 36 wherein an outer surface of each of the jaw members are used to separate vertebral bodies during minimal access spinal surgery.

40. The device of claim 39 wherein the jaw members are adapted to give mechanical support to the spinal column or body structure, as a cage, or other vertebral support means, is deployed through the lumen of the instrument into the space provided by the retracted jaw members.

41. The device of claim 1 wherein the jaw members act as platforms for diagnostic or therapeutic modalities selected from the group comprising ultrasound, lithotripsy, radiotherapy, radiofrequency, unipolar and dipolar electrocautery, stapler-cutters and/or for the application of clips.

42. The device of claim 1 wherein the device includes a calibrated measuring scale, a cutting blade mounted to one jaw member and a receptacle on the other jaw member adapted to receive the cutting blade on closure of the jaw members, the measuring scale allowing a user to determine the dimensions of the cut being made to tissue grasped by the jaw members.

43. The device of claim 1 wherein an ultrasonic emitter is incorporated into the first jaw member, and an ultrasonic receiver is incorporated into the second jaw member.

44. The device of claim 1 wherein a pulse-echo ultrasound transducer/receiver is incorporated into the first jaw member, while the second jaw member is used to secure tissue between the jaw members.

45. The device of claim 1 wherein a compliant extension member having a longitudinal axis, and a distal end extends from each of the distal ends of the jaw members.

* * * * *